(12) United States Patent
Garcia

(10) Patent No.: US 11,733,242 B2
(45) Date of Patent: Aug. 22, 2023

(54) BIOMARKERS AND METHODS OF USE FOR RADIATION-INDUCED LUNG INJURY

(71) Applicant: Arizona Board of Regents on Behalf of the University of Arizona, Tucson, AZ (US)

(72) Inventor: Joe G. N. Garcia, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 516 days.

(21) Appl. No.: 16/670,880

(22) Filed: Oct. 31, 2019

(65) Prior Publication Data

US 2020/0132689 A1 Apr. 30, 2020

Related U.S. Application Data

(60) Provisional application No. 62/896,483, filed on Sep. 5, 2019, provisional application No. 62/753,802, filed on Oct. 31, 2018.

(51) Int. Cl.
| | | |
|---|---|---|
| *G01N 33/573* | (2006.01) | |
| *C07K 16/40* | (2006.01) | |
| *G01N 33/50* | (2006.01) | |
| *G01N 33/534* | (2006.01) | |

(52) U.S. Cl.
CPC ........... *G01N 33/573* (2013.01); *C07K 16/40* (2013.01); *G01N 33/5044* (2013.01); *G01N 33/534* (2013.01); *C12Y 204/02012* (2013.01); *G01N 2458/00* (2013.01); *G01N 2800/40* (2013.01)

(58) Field of Classification Search
CPC ............. G01N 33/573; G01N 33/5044; G01N 33/534; G01N 2458/00; G01N 2800/40; G01N 2800/12; G01N 2800/50; G01N 2800/52; G01N 33/6893; C07K 16/40; C12Y 204/02012
See application file for complete search history.

(56) References Cited

U.S. PATENT DOCUMENTS

2011/0020364 A1 1/2011 Garcia

FOREIGN PATENT DOCUMENTS

| | | |
|---|---|---|
| WO | 2011/109650 A1 | 9/2011 |
| WO | 2017/041114 A2 | 3/2017 |
| WO | WO 2018/191747 | 10/2018 |
| WO | WO 2018/191751 | 10/2018 |
| WO | WO 2021/026487 | 2/2021 |
| WO | WO 2021/026508 | 2/2021 |
| WO | WO 2022/032135 | 2/2022 |

OTHER PUBLICATIONS

Liu et al., Cell Biol. International, 33:19-30, 2009 (Year: 2009).*
Moreno-Vinasco et al., Am J Respir Cell Mol Biol., 51(2):22-228, Aug. 2014 (Year: 2014).*
Ye et al., Am J Respir Crit Care Med. 171(4):361-70; Epub Dec. 3, 2004 (Year: 2004).*
Cheung et al., Acute Lung Injury, Practical Pulmonary Pathology: A Diagnostic Approach: 125-146.e3; published online Nov. 5, 2017 (Year: 2017).*
Adyshev et al., Mechanical Stress Induces Pre-B-cell Colony-Enhancing Factor/NAMPT Expression via Epigenetic Regulation by miR-374a and miR-568 in Human Lung Endothelium, American Journal of Respiratory Cell and Molecular Biology, vol. 50, No. 2, Feb. 2014 (Year: 2014).*
Camp et al., Unique Toll-Like Receptor 5 Activation by NAMPT/PBEF Induces NFkappaB Signaling and Inflammatory Lung Injury, Nature Scientific Reports, 5:13135, published Aug. 14, 2015 (Year: 2015).*
ClinicalTrials.gov Identifier: NCT00003979, completed Jul. 2012 (Year: 2012) Retrieved Online from: <https://beta.clinicaltrials.gov/study/NCT00003979> Retrieved on: Nov. 17, 2022.*
Xiang Bin et al: "Nicotinamide 1-17,Phosphoribosyltransferase Upregulation by 24-32 Phenylephrine Reduces Radiation Injury in Submandibular Gland", International Journal of Radiation:Oncology Biology Physics, Pergamon Press, USA,vol. 96, No. 3,Jul. 1, 2016 (Jul. 1, 2016),pp. 538-546, XP029743870.
International Search Report issued in connection with corresponding International Application No. PCT/IB2019/059379 dated Feb. 14, 2020.
International Preliminary Report on Patentability for Application No. PCT/IB2019/059379 dated Apr. 27, 2021.

* cited by examiner

Primary Examiner — Kimberly Ballard
Assistant Examiner — Stacey N MacFarlane
(74) Attorney, Agent, or Firm — Womble Bond Dickinson (US) LLP

(57) ABSTRACT

The present disclosure is directed to methods (e.g., in vitro methods) for use of nicotinamide phosphoribosyltransferase (NAMPT) as a biomarker in radiation-induced lung injury (RILI). Provided herein is an in vitro method for the diagnosis, prognosis, and/or monitoring of RILI in a human subject by providing a tissue or plasma sample from the subject and detecting the level of NAMPT therein, wherein a higher level of NAMPT in the tissue or plasma sample from the subject compared to a healthy control or a reference value is indicative for the presence of RILI in the subject. Further provided herein is a method of detecting NAMPT in a human subject by obtaining a biological sample from the subject, detecting the presence of NAMPT in the sample by contacting the sample with a capture agent that specifically binds NAMPT, and detecting binding between NAMPT and the capture agent.

20 Claims, 23 Drawing Sheets
(2 of 23 Drawing Sheet(s) Filed in Color)
Specification includes a Sequence Listing.

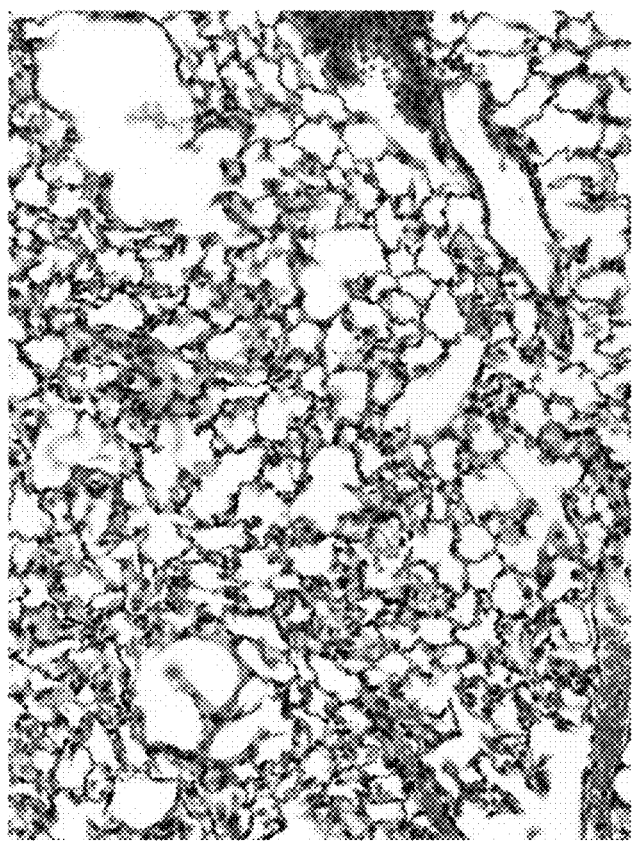
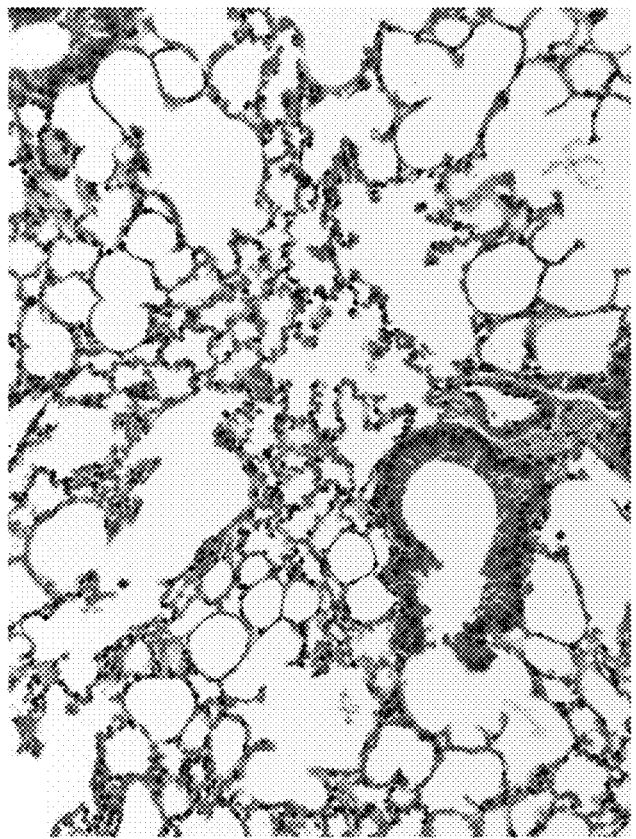
FIG. 4

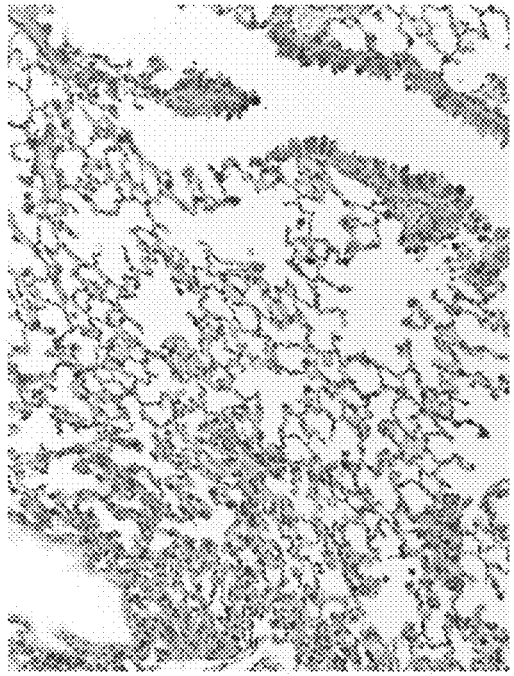
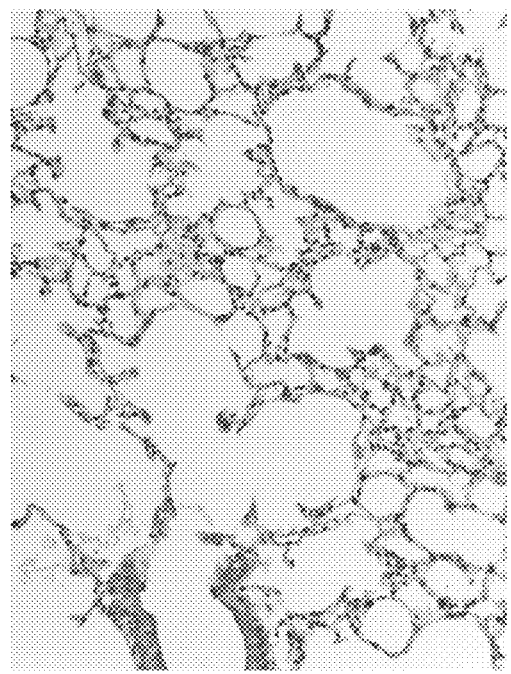
FIG. 5A

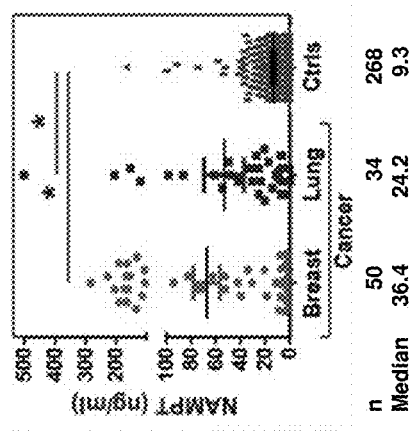
FIG. 14B
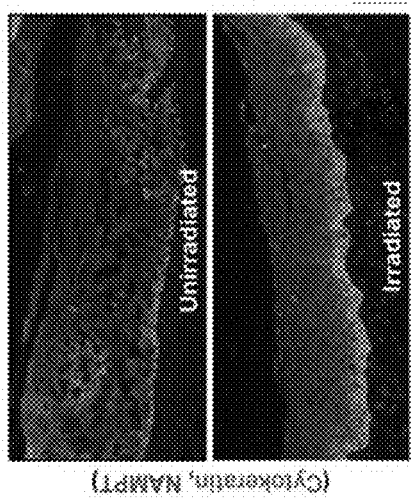
FIG. 14A
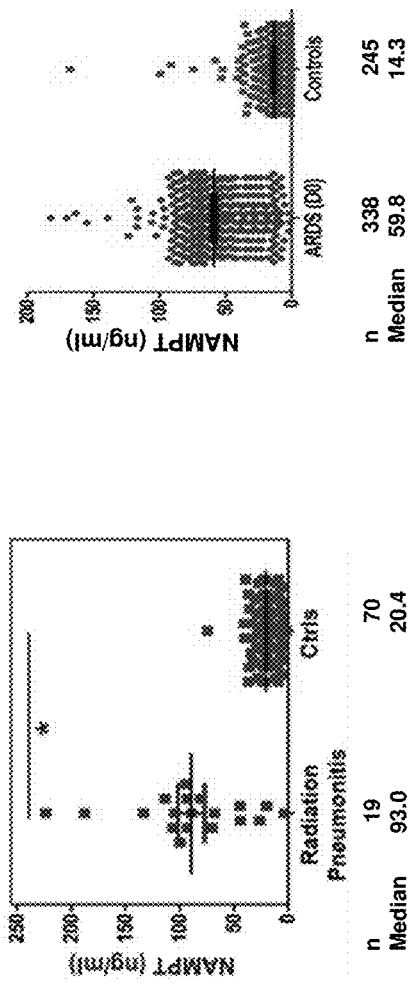
FIG. 14D
FIG. 14C

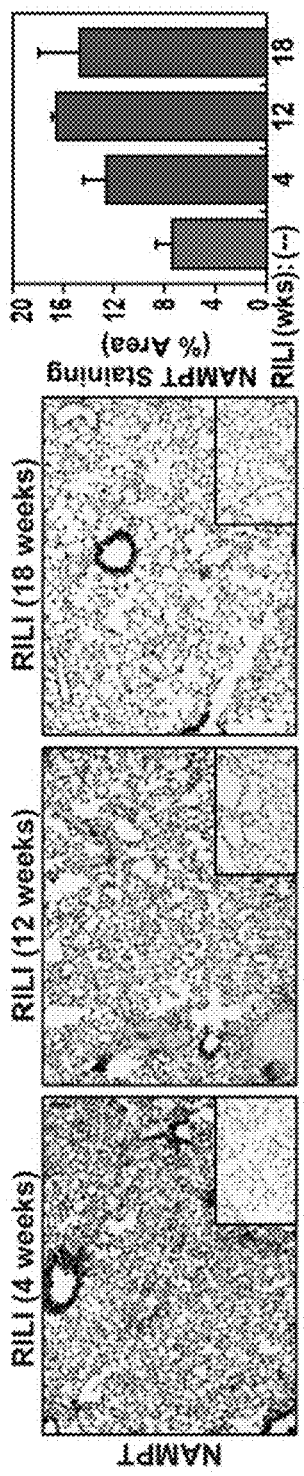

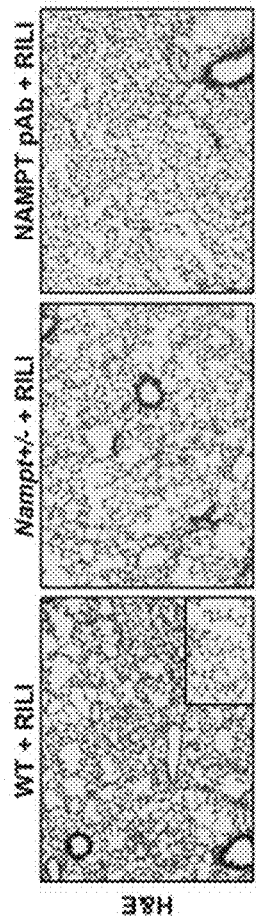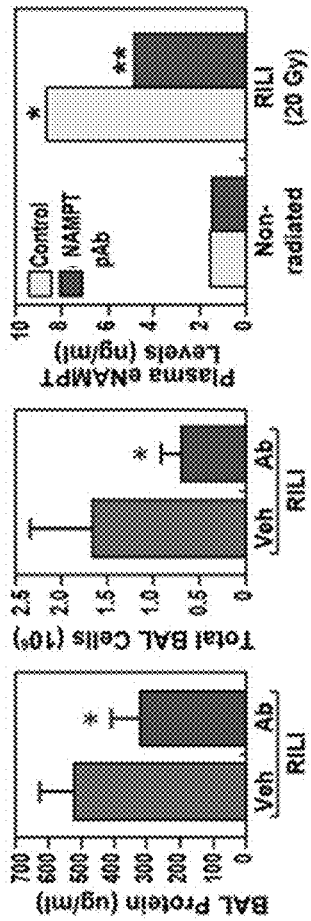

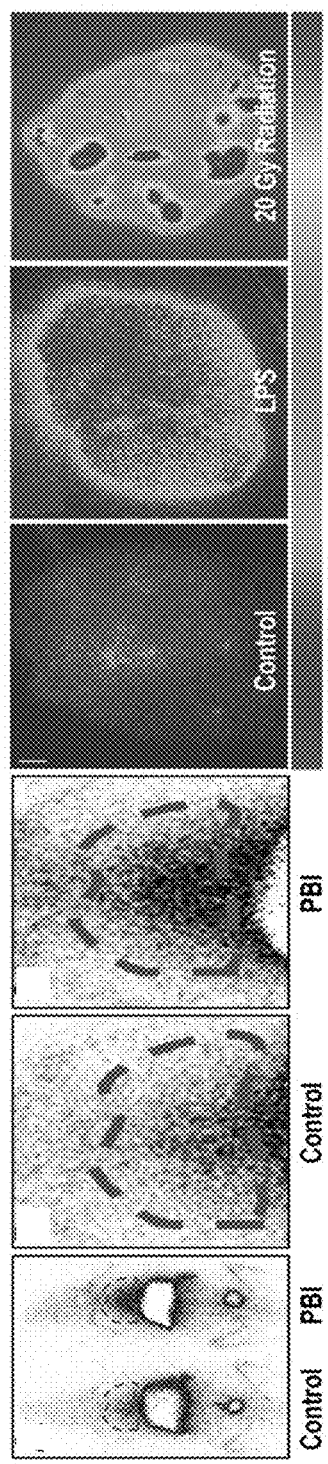

BIOMARKERS AND METHODS OF USE FOR RADIATION-INDUCED LUNG INJURY

RELATED APPLICATIONS

This application claims the benefit of priority to U.S. Provisional Application No. 62/753,802, filed on Oct. 31, 2018, and U.S. Provisional Application No. 62/896,483, filed on Sep. 5, 2019. The contents of these priority applications is hereby incorporated by reference herein.

STATEMENT REGARDING FEDERALLY SPONSORED RESEARCH AND DEVELOPMENT

This invention was made with government support under NIH Grant Nos. R01 HL094394, P01 HL134610, and R42 HL145930, awarded by the National Institutes of Health. The U.S. Government has certain rights in the invention.

SEQUENCE LISTING

The instant application contains a Sequence Listing which has been submitted electronically in ASCII format and is hereby incorporated by reference in its entirety. Said ASCII copy, created on Oct. 30, 2019, is named A105818_1010US_SL.txt and is 10,322 bytes in size.

BACKGROUND

Development of radiation-induced lung injury (RILI) is a disabling, and potentially fatal toxicity in individuals (e.g., cancer patients) undergoing thoracic radiotherapy or in individuals exposed to ionizing radiation (IR), e.g., from a nuclear incident. Of the two major components of RILI, the most prominent is radiation pneumonitis, a sub-acute complication, occurring 4-20 weeks post IR exposure, induced by profound inflammatory responses to IR. Risk factors contributing to the development of radiation pneumonitis are multifactorial but include overall radiation dose, dose-rate fraction size (daily dose increment), volume of lung irradiated, co-morbid factors (e.g., emphysema) and unknown genetic factors. Although estimates vary, radiation pneumonitis generally occurs in ~10% of patients after IR lung exposure including 5-15% of lung cancer patients receiving radiotherapy and ~2-3% of breast cancer patients with focal radiation pneumonitis when receiving postoperative radiotherapy following breast-conserving surgery. The spectrum of radiation pneumonitis severity ranges from mild, self-limited nonspecific respiratory symptoms to severe respiratory insufficiency requiring mechanical ventilation, with significant disability or death. In contrast, the second RILI component, radiation-induced lung fibrosis (RILF), is a late phase, delayed toxicity developing 6-24 months after IR exposure that can result in significant respiratory compromise, disability and death if the regions of fibrosis are extensive. Unfortunately, the development of RILF with diminished lung function limits the use of radiation dose that is required for effective tumor cell killing. RILF pathophysiology incorporates sustained inflammation, cytokine release, and microvascular changes due to pro-angiogenic and pro-fibrogenic stimuli. Management of RILF has limited options, consisting primarily of supportive care. To date, there are no validated therapies available for limiting RILF development or severity.

Recent nuclear accidents, such as the Fukushima incident of 2011 and potential acts of terrorism, have heightened concern for catastrophic IR exposure. Not surprisingly, acute, high-dose IR exposure produces acute-subacute-chronic inflammation, with eventual potentially fatal multi-organ failure, including pneumonitis and RILF. Over 50% of the victims involved in radiation accidents suffer RILI, with a single 8 Gy exposure causing pneumonitis in ~30% of patients, at times with fatal results. Unfortunately, no RILI countermeasures currently exist in the strategic national stockpile, a serious unmet medical and societal need.

The pathobiology of RILI due to either whole thorax lung irradiation (WTLI), total body irradiation (TBI) or partial body irradiation (PBI) is complex and includes the deleterious effects of unchecked inflammation (e.g., reactive oxygen species, cytokines, inflammatory cells, etc.), which increase vascular permeability, impair gas transfer, and promote fibrosis. Although Toll-like receptors (TLRs) and cytokines (IL-1β, TNF-α, IL-4, etc.) are contributors to RILI development, experimental and clinical strategies to neutralize IR-induced proinflammatory cytokine effects or to block inflammatory cell infiltration have been disappointing. Therapies, such as angiotensin-converting-enzyme inhibitors (e.g., Lisinopril and Captopril), pentoxyphylline, and antioxidants (e.g., amifostine), while showing promise in preclinical models, failed to show substantial clinical benefit in humans. Also, only a few of these have actually been tested in large animal models. Usefulness of high dose corticosteroids, which is the standard of care for RILI, remains controversial. Despite acute efficacy, steroid usage presents long term complication including poor outcomes, the need for sustained steroid treatment and frequent, potentially fatal relapses ("recall" pneumonitis). Multiple studies found little benefit from prophylactic steroid administration. Preclinical studies found reduced lethality in IR-exposed mice while on prednisolone (10 mg/kg/day), and steroid withdrawal resulted in accelerated mortality eventually comparable to untreated mice with prolongation of the duration of pneumonitis. Also, early withdrawal exacerbated the severity of the pneumonitis. Thus, absence of a consensus for steroid usage in RILI, its limited efficacy, and serious adverse effects (potentially fatal relapses) mandate a search for safer, more effective therapeutic strategies for RILI, which is a serious unmet need.

SUMMARY OF INVENTION

The present disclosure is directed to methods (e.g., in vitro methods) for use of nicotinamide phosphoribosyltransferase (NAMPT) as a biomarker in radiation-induced lung injury (RILI).

A first aspect provides an in vitro method for the diagnosis, prognosis, and/or monitoring of RILI in a human subject that includes the steps of: (a) providing a tissue or plasma sample from the human subject, (b) detecting the level of NAMPT in the tissue or plasma sample, wherein a higher level of NAMPT in the tissue or plasma sample from the human subject as determined in step (b) compared to a healthy control or a reference value is indicative for the presence of RILI in the human subject.

In some embodiments of the above aspect, step (b) includes detecting the level of NAMPT protein. In certain embodiments, the level of NAMPT protein is detected by autoradiography. In certain embodiments, the level of NAMPT protein is detected by western blot analysis. In certain embodiments, the level of NAMPT protein is detected by immunohistochemistry. In certain embodiments, the level of NAMPT protein is detected by or ELISA.

In some embodiments, the level of NAMPT protein is detected by an anti-NAMPT antibody. In certain embodiments, the anti-NAMPT antibody is radiolabeled.

In other embodiments of the above aspect, step (b) includes detecting the level of NAMPT mRNA. In certain embodiments, the level of NAMPT mRNA is detected by RT-PCR. In particular embodiments, the level of NAMPT mRNA is detected by a primer pair that is complimentary to all or a portion of the nucleic acid sequence of SEQ ID NO: 1.

In some embodiments, the human subject shows symptoms of RILI.

In some embodiments, the human subject is at a risk of developing RILI. In certain embodiments, the human subject is a cancer patient undergoing radiotherapy. In particular embodiments, the human subject is a cancer patient undergoing thoracic radiotherapy. In certain embodiments, the human subject is exposed to ionizing radiation (IR).

In some embodiments of the above aspect, the healthy control or reference value is a level of NAMPT expression in a control subject. In certain embodiments, the control subject is a subject without RILI. In particular embodiments, the control subject is a subject without any lung disease.

In some embodiments of the aforementioned aspect, the tissue is lung tissue. In some embodiments, the tissue is thoracic tissue. In some embodiments, the tissue is tonsillar tissue.

Another aspect provides a method of detecting NAMPT in a human subject by: (a) obtaining a biological sample from the human subject; (b) detecting whether NAMPT is present in the biological sample by contacting the biological sample with a capture agent that specifically binds NAMPT; and (c) detecting binding between NAMPT and the capture agent.

In some embodiments of the aforementioned aspect, the capture agent detects NAMPT protein and the binding between NAMPT and the capture agent in step (c) is detected by autoradiography. In some embodiments of the aforementioned aspect, the capture agent detects NAMPT protein and the binding between NAMPT and the capture agent in step (c) is detected by western blot analysis. In some embodiments of the aforementioned aspect, the capture agent detects NAMPT protein and the binding between NAMPT and the capture agent in step (c) is detected by IHC. In some embodiments of the aforementioned aspect, the capture agent detects NAMPT protein and the binding between NAMPT and the capture agent in step (c) is detected by or ELISA.

In some embodiments of the above aspect, the capture agent is an anti-NAMPT antibody. In certain embodiments, the anti-NAMPT antibody is radiolabeled.

In some embodiments of the aforementioned aspect, the capture agent detects NAMPT mRNA and the binding between NAMPT and the capture agent in step (c) is detected by RT-PCR. In certain embodiments, the capture agent is a primer pair that is complimentary to all or a portion of the nucleic acid sequence of SEQ ID NO: 1.

In some embodiments, the human subject shows symptoms of RILI.

In some embodiments, the human subject is at a risk of developing RILI. In certain embodiments, the human subject is a cancer patient undergoing radiotherapy. In particular embodiments, the human subject is a cancer patient undergoing thoracic radiotherapy. In certain embodiments, the human subject is exposed to ionizing radiation (IR).

In some embodiments of the above aspect, the method further includes (d) comparing level of NAMPT in the human subject to a healthy control or a reference value, wherein a higher level of NAMPT in the biological sample from the human subject compared to the healthy control or reference value is indicative for the presence of RILI in the human subject.

In some embodiments, the healthy control or reference value is a level of NAMPT expression in a control subject. In certain embodiments, the control subject is a subject without RILI. In particular embodiments, the control subject is a subject without any lung disease.

In some embodiments of the above aspect, the biological sample is a tissue or plasma. In certain embodiments, the tissue is lung tissue. In certain embodiments, the tissue is thoracic tissue. In certain embodiments, the tissue is tonsillar tissue.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 3A is a graph showing the count of BAL macrophages in lung tissues of irradiated mice at the indicated times. Also shown in the graph are counts of BAL macrophages in lung tissues of non-irradiated control mice, and mice that were exposed to 0.1 mg/kg LPS. *indicates p=0.01

FIG. 3B is a graph showing the count of BAL PMNs in lung tissues of irradiated mice at the indicated times. Also shown in the graph are counts of BAL PMNs in lung tissues of non-irradiated control mice, and mice that were exposed to 0.1 mg/kg LPS. * indicates p=0.005

FIG. 4 provides micrographs of H&E staining of lung tissue from non-irradiated mice (left panel), and of murine lung tissue at 1-week post radiation (20 Gy) exposure (right panel).

FIGS. 5A-5B depict results from analysis of NAMPT expression in murine lung tissues following exposure to 20 Gy radiation. FIG. 5A provides micrographs of NAMPT staining of lung tissue from non-irradiated mice (left panel), and of murine lung tissue at 1-week post radiation exposure (right panel). FIG. 5B is a micrograph showing NAMPT staining in pneumocytes and macrophages in a section of murine lung tissue at 1-week post radiation exposure.

FIGS. 14A-14D are graphical depictions of the results from analysis of the effects of radiation on NAMPT expression in human tissues and blood. FIG. 14A provides micrographs showing immunohistochemical (IHC) staining for NAMPT in human tonsillar epithelial tissue that was either non-irradiated (upper panel) or exposed to 8 Gy ionizing radiation (IR) for 24 hours (lower panel). FIG. 14B is a graph depicting plasma level of NAMPT in control subjects (n=268) or in subjects undergoing radiotherapy for breast cancer (n=50) or lung cancer (n=34). *indicates $p<0.0001$ FIG. 14C is a graph depicting plasma level of NAMPT in control subjects (n=70) or in patients with radiation pneumonitis (n=19). * indicates $p<0.001$ FIG. 14D is a graph depicting plasma level of NAMPT in control subjects (n=245) or in patients with radiation-induced acute respiratory distress syndrome (ARDS).

FIGS. 15A-15D are graphical depictions of NAMPT expression in lung tissues of WT C57/B6 mice that were exposed to 20 Gy whole thorax lung irradiation (WTLI). FIG. 15A is a micrograph showing NAMPT expression in lung tissue of WTLI-exposed mice at 4 weeks post WTLI exposure. Also shown in the inset is a micrograph depicting NAMPT expression in lung tissue of sham-exposed mice (non-irradiated mice). FIG. 15B is a micrograph showing NAMPT expression in lung tissue of WTLI-exposed mice at 12 weeks post WTLI exposure. Also shown in the inset is a micrograph depicting NAMPT expression in lung tissue of sham-exposed mice (non-irradiated mice). FIG. 15C is a micrograph showing NAMPT expression in lung tissue of WTLI-exposed mice at 18 weeks post WTLI exposure. Also shown in the inset is a micrograph depicting NAMPT expression in lung tissue from sham-exposed mice (non-irradiated mice). FIG. 15D is a graphical depiction of NAMPT expression (% area) in lung tissue of WTLI-exposed mice at 4, 12, and 18 weeks post WTLI exposure. Also depicted in the graph as negative control is NAMPT expression in lung tissue of sham-exposed mice (non-irradiated mice).

FIG. 16A is a graph depicting the amount of BAL protein in lung tissues of WT or NAMPT heterozygous mice 4 weeks after 20 Gy WTLI exposure. Also depicted in the graph is the amount of BAL protein in lung tissues of non-irradiated WT or NAMPT heterozygous mice. FIG. 16B is a graph depicting the count of BAL cells in lung tissues of WT or NAMPT heterozygous mice 4 weeks after 20 Gy WTLI exposure. Also depicted in the graph is the count of BAL cells in lung tissues of non-irradiated WT or NAMPT heterozygous mice. * indicates $p<0.05$ FIGS. 17A-17E are graphical depictions of lung injury and inflammation, BAL protein level, count of BAL cells, and plasma NAMPT level after 4 weeks of WTLI exposure in WT mice that were exposed to 20 Gy WTLI, WT mice that were exposed to 20 Gy WTLI and treated with either an anti-NAMPT pAb or vehicle control, or NAMPT heterozygous mice (Nampt$^{+/-}$) that were exposed to 20 Gy WTLI. FIG. 17A is a micrograph showing H&E staining in lung tissue of WTLI-exposed WT mice. Also shown in the inset is a micrograph showing H&E staining in lung tissue of sham-exposed mice (non-irradiated mice). FIG. 17B is a micrograph showing H&E staining in lung tissue of WTLI-exposed NAMPT heterozygous mice. FIG. 17C is a micrograph showing H&E staining in lung tissue of WTLI-exposed WT mice that were treated with an anti-NAMPT pAb. FIG. 17D is a graphical depiction of the amount of BAL protein (FIG. 17D, left panel) and the count of BAL cells (FIG. 17D, right panel) in lung tissues of WTLI-exposed WT mice that were treated with either an anti-NAMPT pAb or a vehicle. FIG. 17E is a graph depicting plasma NAMPT level in WTLI-exposed ("RILI") WT mice that were treated with either an anti-NAMPT pAb or a vehicle ("Control"). Also depicted in the graph is plasma NAMPT level in to sham-IR exposed ("Non-radiated") mice. * indicates $p<0.05$ FIG. 18A is a micrograph showing H&E staining in lung tissue of WTLI-exposed WT mice. FIG. 18B is a micrograph showing H&E staining in lung tissue of WTLI-exposed WT mice that were treated with an anti-NAMPT pAb. FIG. 18C is a micrograph showing collagen deposition, as detected by Trichrome staining, in lung tissue of WTLI-exposed WT mice. FIG. 18D is a micrograph showing collagen deposition, as detected by Trichrome staining, in lung tissue of NAMPT heterozygous mice. FIG. 18E is a graphical depiction of western blot analyses of the expression of SMA and IL-6 after 12 weeks of WTLI exposure in lung tissues of WT or NAMPT heterozygous mice that were exposed to 20 Gy WTLI (FIG. 18E, left panel), or expression of SMA after 18 weeks of WTLI exposure in lung tissues of WT mice that were exposed to 20 Gy WTLI and treated in absence or presence of an anti-NAMPT pAb (FIG. 18E, right panel). Also depicted in FIG. 18E is the western blot analyses of the expression of vinculin as a loading control.

FIG. 19A is a graph depicting lung injury score in control mice or in mice from LPS-induced "one hit" lung injury model that were treated with an anti-NAMPT pAb or a humanized anti-NAMPT antibody (NN, SS, K, N, XX, P, or UU). FIG. 19B is a graph depicting lung injury score in control mice or in mice from LPS/VILI-induced "two hit" lung injury model that were treated with an anti-NAMPT pAb or a humanized anti-NAMPT antibody (NN, SS, K, N, XX, P, or UU). FIG. 19C provides micrographs showing H&E staining of lung tissues of mice from LPS/VILI-induced "two hit" lung injury model that were treated in presence (FIG. 19C, lower panel) or absence (FIG. 19C, upper panel) of the humanized anti-NAMPT antibody P.

FIGS. 21A-21F are graphical depictions of detection of NAMPT expression by a radiolabeled anti-NAMPT monoclonal antibody (mAb) probe. FIG. 21A is an autoradiograph depicting detection of NAMPT expression by the $^{99m}$Tc-labeled anti-NAMPT mAb probe in a control mouse (left panel) and in a mouse exposed to 8 Gy partial body irradiation (PBI) at 2 weeks post irradiation (right panel). FIG. 21B provides a magnified image of FIG. 21A (left panel) that depicts detection of NAMPT expression by the $^{99m}$Tc-labeled anti-NAMPT mAb probe in lung tissues of a control mouse. FIG. 21C provides a magnified image of FIG. 21A (right panel) that depicts detection of NAMPT expression by the $^{99m}$Tc-labeled anti-NAMPT mAb probe in lung tissues of a mouse exposed to 8 Gy PBI at 2 weeks post irradiation. FIG. 21D is an autoradiographic image depicting detection of NAMPT expression by the $^{99m}$Tc-labeled anti-NAMPT mAb probe in lung tissues of control mice. FIG. 21E is an autoradiographic image depicting detection of NAMPT expression by the $^{99m}$Tc-labeled anti-NAMPT mAb probe in lung tissues of LPS-challenged mice 24 hours after intratracheal injection of LPS. FIG. 21F is an autoradiographic image depicting detection of NAMPT expression by the $^{99m}$Tc-labeled anti-NAMPT mAb probe in lung tissues of WTLI-exposed mice 5 days after 20 Gy WTLI exposure.

DEFINITIONS

Figure 1:
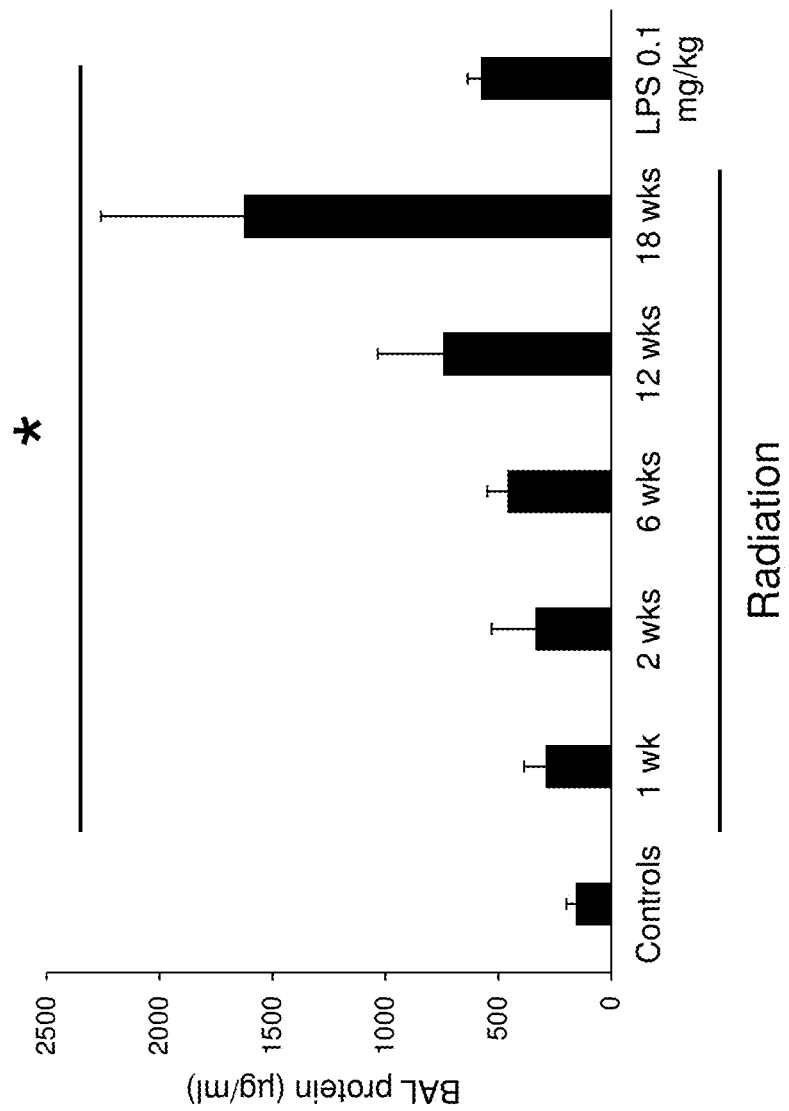
FIG. 1 is a graph depicting the effects of radiation (20 Gy) on the amount of BAL protein in lung tissues of mice at weeks 1, 2, 6, 12, and 18 post radiation exposure. Also shown in the graph are amounts of BAL protein in lung tissues of non-irradiated control mice, and mice that were exposed to 0.1 mg/kg LPS. * indicates p=0.007
Figure 2:
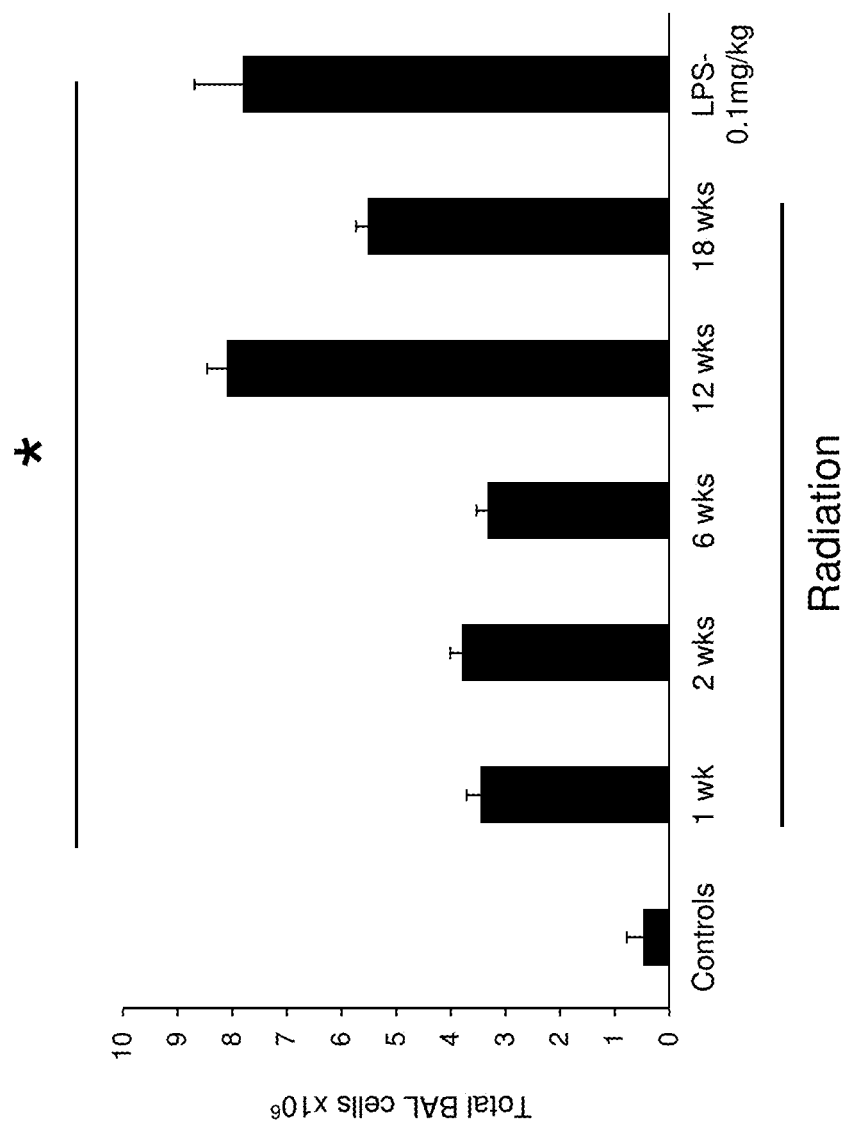
FIG. 2 is a graph depicting the effects of radiation (20 Gy) on the count of BAL-expressing cells (BAL cells) in lung tissues of mice at weeks 1, 2, 6, 12, and 18 post radiation exposure. Also shown in the graph are counts of BAL cells in lung tissues of non-irradiated control mice, and mice that were exposed to 0.1 mg/kg LPS. * indicates p=0.007
Figure 3A:
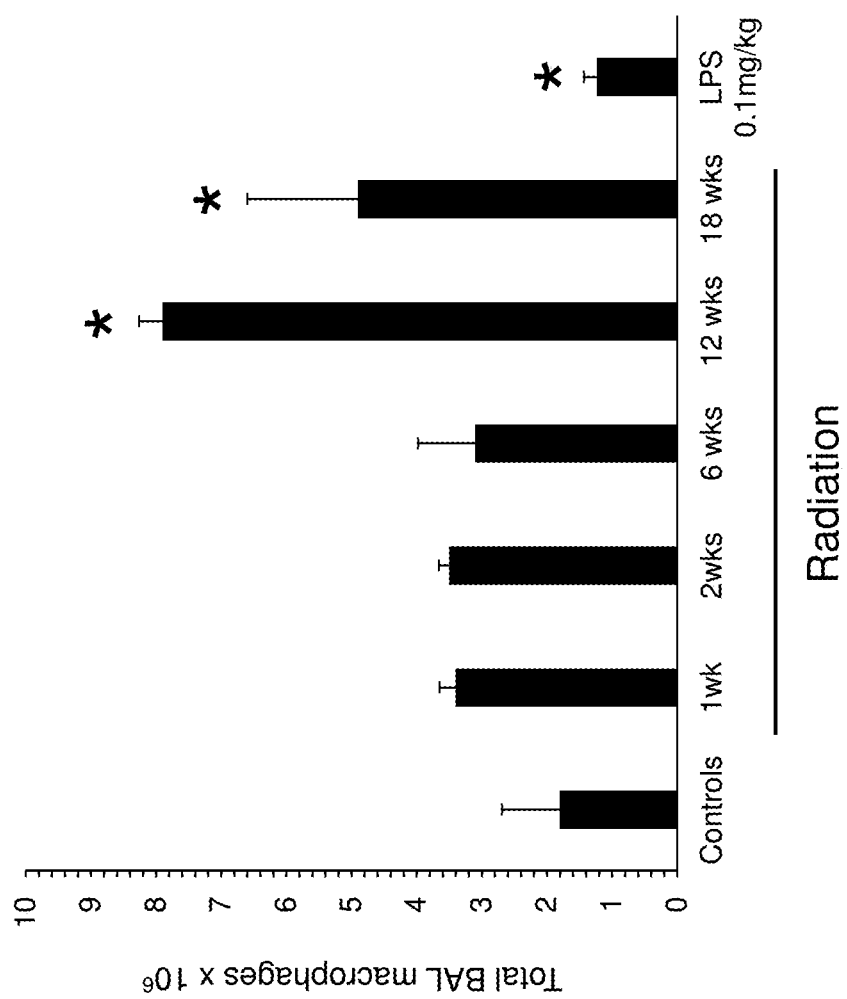
FIGS. 3A-3B are graphical representations of the effects of radiation (20 Gy) on the count of BAL-expressing macrophages (BAL macrophages) and BAL-expressing PMNs (BAL PMNs) in lung tissues of mice at weeks 1, 2, 6, 12, and 18 post radiation exposure.
Figure 3B:
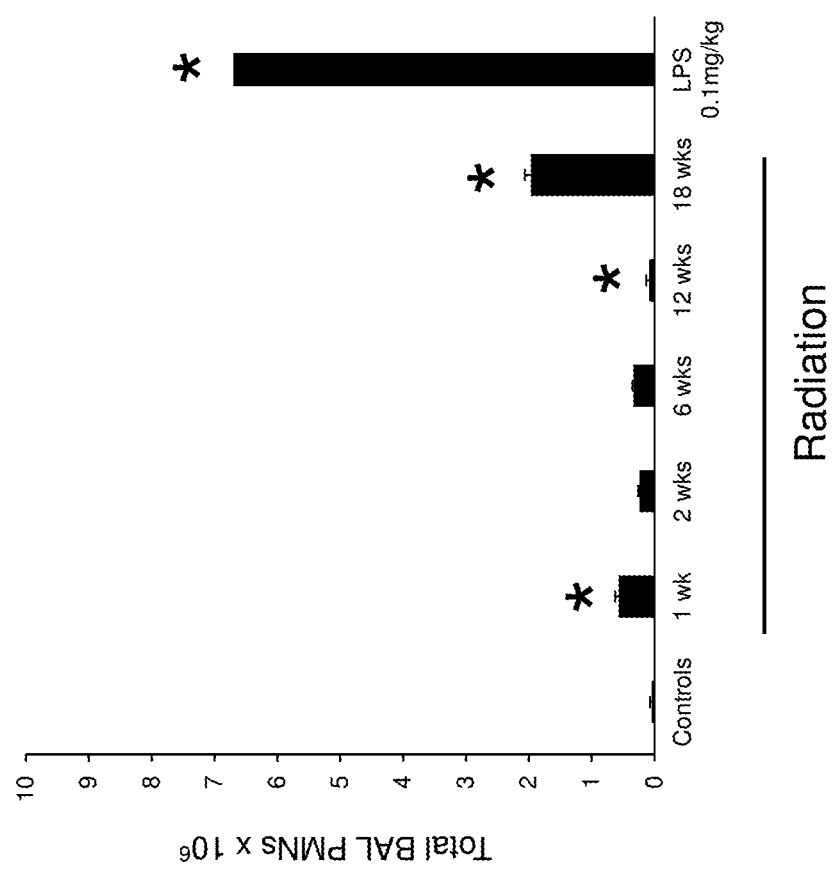

As used herein, the term "polynucleotide" refers to a nucleic acid molecule, RNA or DNA, that has been isolated free of total genomic nucleic acid.

As used interchangeably herein, the terms "NAMPT polynucleotide" or "polynucleotide encoding NAMPT" refer to a NAMPT-encoding nucleic acid molecule that has been isolated essentially or substantially free of total genomic nucleic acid to permit hybridization and amplification, but is not limited to such. Therefore, a "polynucleotide encoding NAMPT" refers to a DNA segment that contains wild-type NAMPT-coding sequence (SEQ ID NO: 1) isolated away from, or purified free from, total mammalian or human genomic DNA. A NAMPT oligonucleotide refers to a nucleic acid molecule that is identical to at least 5 contiguous nucleotides of a NAMPT-encoding sequence, such as identical to at least 5 contiguous nucleotides of SEQ ID NO: 1, which is the cDNA sequence encoding human NAMPT. A sequence complimentary to NAMPT polynucleotide or oligonucleotide, as referred to herein, may be used in some embodiments to detect expression of human NAMPT in a sample (e.g., a biological sample) from a subject (e.g., a test subject).

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human NAMPT or a portion thereof. Typically, at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes. In some embodiments, pairs of primers designed to selectively hybridize to a nucleic acid, such as nucleic acid corresponding to SEQ ID NO: 1 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The term "cDNA" is intended to refer to DNA prepared using RNA as a template. The advantage of using a cDNA, as opposed to genomic DNA or an RNA transcript is stability and the ability to manipulate the sequence using recombinant DNA technology. Moreover, a cDNA may be advantageous because it represents coding regions of a polypeptide and eliminates introns and other regulatory regions. In certain embodiments, nucleic acids are complementary or identical to cDNA encoding sequences, such as a NAMPT sequence.

The term "gene" is used herein for simplicity to refer to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants.

The term "NAMPT gene" or "NAMPT protein," as used herein, refers to any naturally occurring variants or mutants, interspecies homologs or orthologs, or man-made variants of human NAMPT gene or NAMPT protein. The DNA sequence for a human wild-type NAMPT mRNA is set forth in GenBank Accession number NM_005746 (provided herein as SEQ ID NO: 1), which encodes a NAMPT protein (e.g., an isoform of NAMPT protein provided herein as SEQ ID NO: 2). A NAMPT protein within the meaning of this application typically has at least about 80%, or 90%, or 95% or higher sequence identity to the human wild-type NAMPT protein.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human NAMPT protein) or the translation of a protein encoded by a polynucleotide sequence. In other words, both mRNA level and protein level encoded by a gene of interest (e.g., human NAMPT gene) are encompassed by the term "gene expression level" in this disclosure.

In this disclosure the term "biological sample" or "sample" includes sections of tissues (e.g., lung tissue, thoracic tissue, tonsillar tissue, etc.), such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, lung biopsy tissue etc. A Biological sample is typically obtained from a eukaryotic organism, which may be a mammal, may be a primate and may be a human subject.

In this disclosure the term "biopsy" refers to the process of removing a tissue (e.g., lung tissue, thoracic tissue, tonsillar tissue, etc.) sample for diagnostic or prognostic evaluation, and to the tissue specimen itself. Any biopsy technique known in the art can be applied to the diagnostic and prognostic methods of the present invention. The biopsy technique applied will depend on the tissue type (e.g., lung tissue, thoracic tissue, tonsillar tissue, etc.) to be evaluated among other factors. Representative biopsy techniques include, but are not limited to, excisional biopsy, incisional biopsy, needle biopsy, surgical biopsy, and bone marrow biopsy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. For the purposes of this application, amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid. Amino acids may include those having non-naturally occurring D-chirality, as disclosed in WO 01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant NAMPT protein used in the method of this invention has at least about 80% sequence identity, preferably about 85%, 90%, 91%, 92%, 93, 94%, 95%, 96%, 97%, 98%, 99%, or 100% identity, to a reference sequence, e.g., a wild-type human NAMPT protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, Proc. Natl. Acad. Sci. USA 89:10915 (1989)).

The BLAST algorithm also performs a statistical analysis of the similarity between two sequences (see, e.g., Karlin and Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette. The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$ by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies. As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

In some embodiments, described herein is an antibody that binds to NAMPT, such as an anti-NAMPT antibody, or an antigen-binding fragment thereof. In certain embodiments, an anti-NAMPT antibody (e.g., a monoclonal antibody or a polyclonal antibody) is used as a detection agent, such as a detection antibody that binds to NAMPT and detects NAMPT (e.g., from a biological sample), such as detects NAMPT in a detection assay (e.g., in western blot analysis, immunohistochemistry analysis, ELISA, and/or autoradiography analyses). In certain embodiments, an anti-NAMPT antibody (e.g., a monoclonal antibody or a polyclonal antibody) is used as a capture agent that binds to NAMPT and detects NAMPT (e.g., from a biological sample), such as detects NAMPT in a detection assay (e.g., in western blot analysis, immunohistochemistry analysis, ELISA, and/or autoradiography analyses). In some embodiments, an antibody that binds to NAMPT, such as an anti-NAMPT antibody, or an antigen-binding fragment thereof is labeled for ease of detection. In some embodiments, an antibody that binds to NAMPT, such as an anti-NAMPT antibody, or an antigen-binding fragment thereof is radiolabeled (e.g., labeled with a radioisotope, such as labeled with $^3$H, $^{125}$I, $^{35}$S, $^{14}$C, or $^{32}$P, $^{99m}$Tc, or the like), enzymatically labelled (e.g., labeled with an enzyme, such as with horseradish peroxidase (HRP)), fluorescent labeled (e.g., labeled with a fluorophore), labeled with a chemiluminescent agent and/or labeled with a compound (e.g., with biotin and digoxigenin).

In some embodiments, an anti-NAMPT antibody is used as an antibody inhibitor. In some embodiments, an antibody inhibitor (e.g., an anti-NAMPT antibody inhibitor) may be considered a neutralizing antibody. Included within the definition of an antibody that binds NAMPT is a NAMPT antibody binding fragment. As used herein, the term "NAMPT binding fragment" or "binding fragment thereof" encompasses a fragment or a derivative of an antibody that still substantially retain its biological activity of inhibiting NAMPT activity. Therefore, the term "antibody fragment" or NAMPT binding fragment refers to a portion of a full length antibody, generally the antigen binding or variable region thereof. Examples of antibody fragments include Fab, Fab'. F(ab')$_2$, and Fv fragments; diabodies; linear antibodies; single-chain antibody molecules, e.g., sc-FV; and multispecific antibodies formed from antibody fragments. Typically, a binding fragment or derivative retains at least 50% of its NAMPT inhibitory activity. Preferably, a binding fragment or derivative retains about or at least about 60%, 70%, 80%, 90%, 95%, 99% or 100% of its NAMPT inhibitory activity. It is also intended that a NAMPT binding fragment can include conservative amino acid substitutions that do not substantially alter its biologic activity.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975), or may be made by recombinant DNA methods (see, e.g., U.S. Pat. No. 4,816,567). The "monoclonal antibodies" may also be isolated from phage antibody libraries using the techniques described in Clackson et al. (1991) and Marks et al. (1991), for example.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Any suitable method for generating monoclonal antibodies may be used. For example, a recipient may be immunized with NAMPT or a fragment thereof. Any suitable method of immunization can be used. Such methods can include adjuvants, other immunostimulants, repeated booster immunizations, and the use of one or more immunization routes.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. For example, an anti-NAMPT antibody (e.g., a radiolabeled (e.g., labeled with a radioisotope, such as labeled with $^3$H, $^{125}$I, $^{35}$S, $^{14}$C, or $^{32}$P, $^{99m}$Tc, or the like) anti-NAMPT antibody, an enzymatically labelled (e.g., labeled with an enzyme, such as with horseradish peroxidase (HRP)) anti-NAMPT antibody, a fluorescent labeled (e.g., labeled with a fluorophore) anti-NAMPT antibody. an anti-NAMPT antibody labeled with a chemiluminescent agent, and/or an anti-NAMPT antibody labeled with a compound) can bind to NAMPT at least about two times the background and does not substantially bind in a significant amount to other proteins present in a biological sample and can be used as a detection agent and/or a capture agent for detection of NAMPT in a biological sample (e.g., in a biological sample from a test subject or a control subject). Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically, a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established normal level or an established standard control. An increase is a positive change that is typically at least about 5%, 10%, 15%, 20%, 25%, 30%, 35%, 40%, 45%, 50%, 55%, 60%, 65%, 70%, 75%, 80%, 85%, 90%, 95%, 97%, 99%, or more, and can be as high as at least about 2-fold or at least about 5-fold or even about 10-fold of the normal or control value. Similarly, a decrease is a negative change that is typically at least about 5%, 10%, 15%, 20%, 25%, 30%, 35%, 40%, 45%, 50%, 55%, 60%, 65%, 70%, 75%, 80%, 85%, 90%, 95%, 97%, 99%, or below the normal or control value. Other terms indicating quantitative changes or differences from a comparative basis, such as "more," "less," "higher," and "lower," are used in this application in the same fashion as described above. For example, higher NAMPT expression in a test subject indicates that the level of NAMPT expression in a biological sample of the test subject is at least about 5%, 10%, 15%, 20%, 25%, 30%, 35%, 40%, 45%, 50%, 55%, 60%, 65%, 70%, 75%, 80%, 85%, 90%, 95%, 97%, 99%, or above the normal level, control level, healthy control level, or reference level of NAMPT expression (e.g., level of NAMPT expression in same type of biological sample from a subject before the onset of RILI or level of NAMPT expression in same type of biological sample from a control subject, such as a healthy control subject (e.g., a subject without RILI and/or a subject without any lung disease)). In contrast, the term "substantially the same" or "substantially lack of change" indicates little to no change in quantity from the standard control value, typically within +10% of the standard control, or within ±5%, 2%, or even less variation from the standard control.

The term "inhibiting" or "inhibition," as used herein, refers to any detectable negative effect on a target biological process, such as cellular signal transduction, cell proliferation, inflammation, expression, and severity of a disease/condition. Typically, an inhibition is reflected in a decrease of at least 5%, 10%, 15%, 20%, 25%, 30%, 35%, 40%, 45%, 50%, 55%, 60%, 65%, 70%, 75%, 80%, 85%, 90%, 95%, 97%, 99%, or more in target process (e.g., expression of NAMPT at either mRNA level or protein level) upon application of an inhibitor (e.g., an anti-NAMPT antibody), when compared to a control where the inhibitor is not applied.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

A "label," "detectable label," or "detectable moiety" is a composition detectable by spectroscopic, photochemical, biochemical, immunochemical, chemical, or other physical means. For example, useful labels include radioisotopes or radiolabels (e.g., $^3$H, $^{125}$I, $^{35}$S, $^{14}$C, or $^{32}$P, $^{99m}$Tc, or the like), fluorescent dyes, fluorophores, chemiluminescent agents, electron-dense reagents, enzymes (e.g., as commonly used in an ELISA, such as HRP), biotin, digoxigenin, or haptens and proteins that can be made detectable, e.g., by incorporating a radioactive component into the peptide or used to detect antibodies specifically reactive with the peptide. Typically, a detectable label is attached to a probe or a molecule (e.g., to an antibody, such as to an anti-NAMPT antibody) with defined binding characteristics (e.g., a polypeptide with a known binding specificity or a polynucleotide), so as to allow the presence of the probe or the molecule and therefore its binding target (e.g., NAMPT as binding target of a labeled anti-NAMPT antibody) to be readily detectable.

"Normal level" or "standard control" or "control level" or "healthy control level" or "reference level" as used interchangeably herein refers to a predetermined amount or concentration of a polynucleotide sequence or polypeptide, e.g., NAMPT genomic DNA, mRNA, or protein, that is present in an established normal disease-free biological sample, e.g., in a biological sample from a subject before the onset of RILI or in a biological sample from a control subject, such as a healthy control subject (e.g., a subject without RILI and/or a subject without any lung disease). The normal level value, standard control value, control level value, healthy control level value, or reference level value is suitable for the use of a method of the present invention, to serve as a basis for comparing the amount of NAMPT genomic DNA, mRNA, or protein that is present in a test sample (e.g., in a biological sample of a test subject). A normal level value, standard control value, control level value, healthy control level value, or reference level value may vary depending on the nature of the sample as well as other factors such as the gender, age, ethnicity of the subjects based on whom such a control value is established.

The term "average," as used in the context of describing a human who is healthy, free of any lung disease (especially RILI) as conventionally defined, refers to certain characteristics, especially the copies of NAMPT genomic sequence or amount of NAMPT mRNA or protein, found in the person's biological sample (e.g., cell, tissue (e.g., lung tissue, tonsillar tissue, thoracic tissue, etc.), or plasma) that are representative of a randomly selected group of healthy humans who are free of any lung diseases (especially RILI) and free of known risk of developing the disease. This selected group should comprise a sufficient number of humans such that the average copy number and average amount of NAMPT mRNA or protein in the biological sample among these individuals reflects, with reasonable accuracy, the corresponding copy number of NAMPT gene and amount of NAMPT mRNA/protein in the general population of healthy humans. In addition, the selected group of humans generally have a similar age to that of a subject (e.g., test subject) whose biological sample is tested for indication of RILI. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human NAMPT genomic DNA, NAMPT mRNA, or NAMPT protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of a NAMPT inhibitor (e.g., an anti-NAMPT antibody) is the amount of said inhibitor to achieve a decreased level of NAMPT mRNA or protein expression or biological activity, such that the symptoms, severity, and/or onset of RILI are reduced, reversed, eliminated, prevented, or delayed in a patient who has been given the NAMPT inhibitor for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, RILI. Subjects also include individuals currently undergoing therapy that seek manipulation of the therapeutic regimen. Subjects or individuals in need of treatment include those that demonstrate symptoms of RILI or are at risk of developing RILI (e.g., cancer patient undergoing thoracic radiotherapy and/or a subject exposed to ionizing radiation (IR), e.g., from a nuclear incident). For example, a subject in need of treatment includes individuals that have suffered relevant symptoms of RILI in the past, those suffering from RILI, and those that have been exposed to a triggering substance or event (e.g., cancer patient undergoing thoracic radiotherapy and/or a subject exposed to IR, e.g., from a nuclear incident). A "subject in need of treatment" may be at any age of life.

As used herein, "test subject" refers to a subject (e.g., a human) who is to be tested for the diagnosis, prognosis, and/or monitoring of RILI by the methods described herein. Test subjects may include subjects that demonstrate symptoms of RILI, and subjects that are at risk of developing RILI (e.g., cancer patient undergoing thoracic radiotherapy and/or a subject exposed to IR, e.g., from a nuclear incident). In some embodiments, a test subject may be an individual that has suffered relevant symptoms of RILI in the past, a subject suffering from RILI, and/or a subject that has been exposed to a triggering substance or event (e.g., cancer patient undergoing thoracic radiotherapy and/or a subject exposed to IR, e.g., from a nuclear incident).

As used herein, "control subject" or "healthy control subject" refers to a subject (e.g., a human) who does not have RILI and/or a subject (e.g., a human) who does not have any lung disease. A biological sample from a control subject or healthy control subject shows normal level, healthy control level, or reference level of NAMPT expression.

"Inhibitors," "activators," and "modulators" of NAMPT protein are used to refer to inhibitory, activating, or modulating molecules, respectively, identified using in vitro and in vivo assays for NAMPT protein binding or signaling, e.g., ligands, agonists, antagonists, and their homologs and mimetics. The term "modulator" includes inhibitors and activators. Inhibitors are agents that, e.g., partially or totally block binding, decrease, prevent, delay activation, inactivate, desensitize, or down regulate the activity of NAMPT protein. In some cases, the inhibitor directly or indirectly binds to NAMPT protein, such as a neutralizing antibody (e.g., a humanized anti-NAMPT monoclonal antibody). Inhibitors, as used herein, are synonymous with inactivators and antagonists. Activators are agents that, e.g., stimulate, increase, facilitate, enhance activation, sensitize or up regulate the activity of NAMPT protein. Modulators include NAMPT protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

The term "promoter," as used here, refers to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

A "diagnosis" or the term "diagnostic" in context of the present invention means identifying the presence or nature of RILI, such as identifying the presence or nature of RILI in a test subject using NAMPT as a biomarker by the methods described herein. Diagnostic methods differ in their sensitivity and specificity. The sensitivity of a diagnostic assay is the percentage of diseased individuals who test positive (percent of true positives). Diseased individuals not detected by the assay are false negatives. Subjects who are not diseased and who test negative in the assay, are termed true negatives. The specificity of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

The term "prognosis" as used herein refers to a forecast as to the probable outcome of RILI as well as the prospect of recovery from RILI as indicated by the nature and symptoms of the case. For example, disclosed herein are methods of forecasting the probable outcome of RILI as well as the prospect of recovery from RILI in test subjects using NAMPT as a biomarker. A negative or poor prognosis is defined by a lower post-treatment survival term or survival rate. Conversely, a positive or good prognosis is defined by an elevated post-treatment survival term or survival rate. Usually prognosis is provided as the time of progression free survival or overall survival.

The term "monitoring progression" means for the purpose of the present invention to observe progression of RILI in a test subject. In some embodiments, a test subject (e.g., a subject with RILI) who is in therapy (e.g., with a NAMPT inhibitor, such as an anti-NAMPT antibody), is regularly monitored during the therapy for the effect of the applied therapy (e.g., effect on the severity of RILI and/or effect on the expression of NAMPT), which allows the medical practitioner to estimate at an early stage during the therapy whether the prescribed treatment is effective or not, and therefore to adjust the treatment regime accordingly.

DETAILED DESCRIPTION OF THE INVENTION

Radiation-induced lung injury (RILI), radiation pneumonitis and radiation fibrosis, are potentially life-threatening consequences of thoracic radiation with an unmet need for reliable RILI biomarkers and novel therapeutic strategies. The contribution of inflammation to the development of RILI supports an approach to reduce the damage signals and ensuing inflammatory burden in IR-exposed individuals.

Nicotinamide Phosphoribosyltransferase (NAMPT)

Nicotinamide phosphoribosyltransferase (NAMPT) is also known as pre-B cell colony enhancing factor (PBEF) or visfatin. The human NAMPT gene (NAMPT) is located on chromosome 7, (segment 7q22.3; base pairs 106,248,285 to 106,286,326). The human cDNA sequence of NAMPT is provided in GenBank Accession number NM_005746, which is hereby incorporated by reference. This sequence also corresponds to SEQ ID NO: 1. The NAMPT gene encodes a protein that exists in two forms, intracellular NAMPT (iNAMPT) and extracellular NAMPT (eNAMPT), with iNAMPT catalyzing nicotinamide adenine dinucleotide (NAD) synthesis. The protein sequence encoded by the NAMPT gene is provided as SEQ ID NO: 2.

NAMPT has been characterized as a proinflammatory cytokine based on its effect on the maturation of B cells (Samal et al., *Mol Cell Biol* 14:1431-1437 (1994)) and has been reported to regulate insulin secretion in beta cells as a systemic NAD biosynthetic enzyme (Revollo et al., *Cell Metab* 6:363-375 (2007)). NAMPT has been shown to increase the production of IL-6, TNF-$\alpha$, and IL-1$\beta$ in CD14$^+$ monocyctes, macrophages, and dendritic cells, enhance the effectiveness of T cells, and be involved in the development of both B and T lymphocytes (Sun et al., *Cytokine & Growth Factor Reviews* 24:433-442 (2013)). A NAMPT enzyme crystal structure is described in detail by Kim et al. (*J Mol Biol* 362:66-77 (2006)). NAMPT is the rate-limiting enzyme in the NAD salvage pathway that converts nicotinamide to nicotinamide mononucleotide in mammals to enable NAD biosynthesis. The mature form of the extracellular NAMPT protein is a homodimer of approximately 120 kDa (Takahashi et al., *J Biochem* 147:95-107 (2010)). It has been established that mutations which reduce or inhibit the function of the NAMPT enzyme can reduce the pathophysiological processes that give rise to disorders such as leukemia and pulmonary arterial hypertension (PAH).

NAMPT has been identified as a ligand for Toll-like receptor 4 (TLR4), a protein that in humans is encoded by the TLR4 gene. TLR4 is a transmembrane protein and a member of the toll-like receptor family, which belongs to the pattern recognition receptor (PRR) family. Activation of TLR4 leads to an intracellular NF-$\kappa$B signaling pathway and inflammatory cytokine production, which is responsible for activating the innate immune system. TLR4 is most well-known for recognizing lipopolysaccharide (LPS), a component present in many Gram-negative bacteria (e.g., *Neisseria* spp.) and select Gram-positive bacteria. Its ligand also includes several viral proteins, polysaccharide, and a variety of endogenous proteins such as low-density lipoprotein, beta-defensins, and heat shock protein. The human TLR4 gene is located on chromosome 9 (segment 9q32-q33) (George) et al., *PLoS ONE* 4(11):e7803 (2009)). Nucleic acid sequences for the human TLR4 gene product are known in the art. See, for example, NCBI Reference Sequence: AAY82268.1, *Homo sapiens* toll-like receptor 4 (TLR4), mRNA. Amino acid sequences of the human TLR4 are known in the art. See, for example, GenBank Accession No. AAY82268.

NAMPT has been identified as a potent pro-inflammatory cytokine with role in the pathophysiology of acute respiratory distress syndrome (ARDS) and ventilator-induced lung injury. Both iNAMPT and eNAMPT have been linked to regulation of metabolism, stress responses, apoptosis, aging, and fibrosis. eNAMPT profoundly amplifies dysregulated inflammatory response that results in organ dysfunction, cytokine storm and death in severe critical illnesses. iNAMPT is a highly druggable therapeutic target in cancer; however, iNAMPT enzymatic inhibitors have failed in Phase II and Phase III clinical cancer trials due to unacceptable toxicity.

The present disclosure is directed to the use of NAMPT as a biomarker in RILI. Also disclosed are methods and compositions for use of NAMPT as a therapeutic target in RILI.

Use of NAMPT as a Biomarker in RILI

Disclosed herein are methods (e.g., in vitro methods) of and compositions for use of NAMPT as a biomarker in RILI. In some embodiments, expression of NAMPT (e.g., DNA, RNA, and/or protein expression of NAMPT) is higher (e.g., by 5% or more, such as by 5%, 10%, 15%, 20%, 25%, 30%, 35%, 40%, 45%, 50%, 55%, 60%, 65%, 70%, 75%, 80%, 85%, 90%, 95%, 97%, 99%, or more) in a subject with RILI compared to the expression of NAMPT in the subject before the onset of RILI or compared to the expression of NAMPT in a control subject, such as a healthy control subject (e.g., a subject without RILI and/or any lung disease). For example, expression of NAMPT (e.g., DNA, RNA, and/or protein expression of NAMPT) may be higher (e.g., by 5% or more, such as by 5%, 10%, 15%, 20%, 25%, 30%, 35%, 40%, 45%, 50%, 55%, 60%, 65%, 70%, 75%, 80%, 85%, 90%, 95%, 97%, 99%, or more) in a tissue (e.g., lung tissue, tonsillar tissue, thoracic tissue, etc.) or in plasma of a subject with RILI compared to the expression of NAMPT in the tissue or plasma of the subject before the onset of RILI or compared to the expression of NAMPT in the tissue or plasma of a control subject, such as a healthy control subject (e.g., a subject without RILI and/or any lung disease).

In some embodiments, increased expression of NAMPT in a tissue (e.g., lung tissue, tonsillar tissue, thoracic tissue, etc.) or in plasma of a subject (e.g., a subject who is at a risk of developing RILI) may indicate occurrence of RILI in the subject. Alternatively, increased expression of NAMPT in a tissue (e.g., lung tissue, tonsillar tissue, thoracic tissue, etc.) or in plasma of a subject (e.g., a subject who is at a risk of developing RILI) may indicate onset of RILI in the subject. Additionally or alternatively, increased expression of NAMPT in a tissue (e.g., lung tissue, tonsillar tissue, thoracic tissue, etc.) or in plasma of a subject may indicate that the subject is at an increased risk of developing RILI. A subject (e.g., a human) who is at a risk of developing RILI may be a cancer patient undergoing thoracic radiotherapy. Additionally or alternatively, a subject (e.g., a human) who is at a risk of developing RILI may be a subject exposed to ionizing radiation (IR), e.g., from a nuclear incident.

In some embodiments, a subject (e.g., a human) with higher than normal level (or standard control level, control level, healthy control level, or reference level) of NAMPT expression in tissue (e.g., lung tissue, tonsillar tissue, thoracic tissue, etc.) or plasma is indicative of a subject with RILI. Additionally or alternatively, a subject (e.g., a human) with higher than normal level of NAMPT expression in tissue (e.g., lung tissue, tonsillar tissue, thoracic tissue, etc.) or plasma is indicative of a subject who is at an increased risk of developing RILI. In some embodiments, normal level (or standard control level, control level, healthy control level, or reference level) of NAMPT expression is the expression level of NAMPT in tissue (e.g., lung tissue, tonsillar tissue, thoracic tissue, etc.) or plasma of a subject before the onset of RILI. In some embodiments, normal level (or standard control level, control level, healthy control level, or reference level) of NAMPT expression is the expression level of NAMPT in tissue (e.g., lung tissue, tonsillar tissue, thoracic tissue, etc.) or plasma of a control subject, such as a healthy control subject (e.g., a subject without RILI and/or any lung disease)).

It is to be contemplated that for the purpose of the presently disclosed methods, NAMPT expression in a biological sample of a test subject (e.g., a subject suspected to have RILI and/or a subject at a risk of developing RILI) is to be compared to the normal level (or standard control level, control level, healthy control level, or reference level) of NAMPT expression in biological sample of the same type (e.g., level of NAMPT expression in biological sample of the same type from a subject before the onset of RILI and/or level of NAMPT expression in biological sample of the same type from a control subject). For example, for the purpose of the presently disclosed methods: NAMPT expression in lung tissue of a test subject is to be compared to the normal level of NAMPT expression in lung tissue; NAMPT expression in tonsillar tissue of a test subject is to be compared to the normal level of NAMPT expression in tonsillar tissue; NAMPT expression in thoracic tissue of a test subject is to be compared to the normal level of NAMPT expression in thoracic tissue; and/or NAMPT expression in plasma of a test subject is to be compared to the normal level of NAMPT expression in plasma.

It is contemplated that one or more standards may be generated in which a normal level of NAMPT expression is defined or identified. That standard may then be referred to as a way of determining whether expression in a given subject (e.g., a test subject, such as a subject suspected to have RILI and/or a subject at a risk of developing RILI) is normal or above normal. The type of standard generated will depend upon the assay or test employed to evaluate NAMPT expression. In some embodiments, a score is assigned to a sample based on certain criteria, and numbers within or above a certain number or range are deemed "above normal." In some embodiments, NAMPT expression is considered above normal if an assay indicates that a particular measurement, amount or level of NAMPT expression is at about or at most about 5%, 10%, 15%, 20%, 25%, 30%, 35%, 40%, 45%, 50%, 55%, 60%, 65%, 70%, 75%, 80%, 85%, 90%, 95%, 97%, 99%, or above the measurement, amount or level observed in tissue or plasma that have normal levels of NAMPT expression (e.g., above the measurement, amount or level observed in tissue or plasma of a subject before the onset of RILI or above the measurement, amount or level observed in tissue or plasma of a control subject (e.g., a subject without RILI and/or a subject without any lung disease)). In preferred embodiments, NAMPT expression is considered above normal if an assay indicates that a particular measurement, amount or level of NAMPT expression is at about or at most about 50%, 55%, 60%, 65%, 70%, 75%, 80%, 85%, 90%, 95%, 97%, 99%, or above the measurement, amount or level observed in tissue or plasma that have normal levels of NAMPT expression (e.g., above the measurement, amount or level observed in tissue or plasma of a subject before the onset of RILI or above the measurement, amount or level observed in tissue or plasma of a control subject (e.g., a subject without RILI)). Alternatively, in some embodiments, NAMPT expression is considered above normal if an assay indicates that a particular measurement, amount or level of NAMPT expression is about or at least about 1, 2, 3, 4, 5, 6, 7, 8, 9, 10, or more standard deviations above the measurement, amount or level of NAMPT observed in cells, tissues or plasma that have normal levels of NAMPT expression. In other cases, NAMPT expression may be considered above normal if a measurement, amount or level of NAMPT is or is about 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or more times greater than the measurement, amount, or level of NAMPT observed in cells, tissues or plasma that have normal levels of NAMPT expression.

Evaluating NAMPT Expression

It is contemplated that NAMPT levels can be assayed from a sample from a subject, such as a test subject (e.g., a subject who is suspected of having RILI and/or a subject who is at increased risk of having RILI). In some embodiments, a sample from a subject refers to a biological sample. In some embodiments, biological sample includes, but is not limited to a tissue biopsy or section (e.g., biopsy or section from lung tissue, tonsillar tissue, thoracic tissue, etc.), blood sample, lavage, swab, scrape, nipple aspirate, or other composition that may be extracted from the body and that contains cells. In other embodiments, biological sample includes plasma. In particular embodiments, a sample from a subject (e.g., a test subject) may contain all or part of a tissue (e.g., lung tissue, tonsillar tissue, thoracic tissue, etc.) biopsy. In further embodiments, a sample from a subject (e.g., a test subject) may contain all or part of a lung tissue biopsy, which may be from a bilateral biopsy or a unilateral biopsy.

Provided herein are methods for evaluating expression of NAMPT in cells, tissues, or plasma, such as in cells, tissues or plasma of a subject (e.g., a test subject). Expression of NAMPT in cells, tissues or plasma can be evaluated by a number of ways that directly or indirectly provide information regarding their expression. Thus, ways of evaluating NAMPT expression include, but are not limited to, assessing or measuring the corresponding protein, assessing or measuring the corresponding transcript, sequencing the corresponding transcript or genomic sequence, and assaying NAMPT activity. NAMPT can be detected in a biological sample (e.g., cell, tissue, plasma) etc. using methods similar to those described in U.S. Pat. No. 9,409,983, which is incorporated herein by reference in its entirety.

I. General Methodology

Practicing the methods disclosed herein utilizes routine techniques in the field of molecular biology. Basic texts disclosing the general methods of use in this disclosure include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett* 22:1859-1862 (1981), using an automated synthesizer, as described in Van Devanter et. al., *Nucleic Acids Res* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J Chrom* 255: 137-149 (1983).

The sequence of interest used in this invention, e.g., the polynucleotide sequence of the human NAMPT gene can be verified using, e.g., the chain termination method for double-stranded templates of Wallace et al., Gene 16: 21-26 (1981).

II. Acquisition of Tissue Samples and Analysis of NAMPT mRNA or DNA

The present disclosure relates to a method (e.g., an in vitro method) of measuring the amount of NAMPT mRNA or NAMPT genomic DNA found in a cell, tissue (e.g., lung tissue, tonsillar tissue, thoracic tissue, etc.) or plasma sample of a subject, as a means to detect the presence, to assess the risk of developing, to diagnose, to prognose, and/or to monitor the progression or treatment efficacy of RILI. Thus, the first steps of practicing the methods of this disclosure (e.g., in vitro methods to use NAMPT as a biomarker for diagnosis, prognosis, and/o monitoring of RILI) are to obtain a cell, tissue or plasma sample from a test subject and extract mRNA or DNA from the sample.

A. Acquisition and Preparation of Samples

A biological sample (e.g., cell, tissue (e.g., lung tissue, tonsillar tissue, thoracic tissue, etc.) or plasma) is obtained from a person to be tested or monitored for RILI using a method of the present disclosure. Biological samples of the same type should be taken from both a test subject (e.g., a subject suspected to have RILI and/or a subject at a risk of developing RILI) and a control subject (e.g., a subject not suffering from RILI and/or any lung disorder). Collection of a biological sample from a subject, such as a test subject is performed in accordance with the standard protocol hospitals or clinics generally follow. An appropriate amount of biological sample (e.g., cell, tissue (e.g., lung tissue, tonsillar tissue, thoracic tissue, etc.) or plasma) is collected and may be stored according to standard procedures prior to further preparation.

The analysis of NAMPT mRNA or DNA found in biological sample of a subject (e.g., test subject) according to the method disclosed herein may be performed using, e.g., cells, tissues, or plasma. The methods for preparing biological samples for nucleic acid extraction are well known among those of skill in the art. For example, tissue of a subject (e.g., test subject) should be first treated to disrupt cellular membrane so as to release nucleic acids contained within the cells.

B. Extraction and Quantitation of DNA and RNA

Methods for extracting DNA from a biological sample are well known and routinely practiced in the art of molecular biology (e.g., described by Sambrook and Russell, Molecular Cloning: A Laboratory Manual 3d ed., 2001). RNA contamination should be eliminated to avoid interference with DNA analysis.

Likewise, there are numerous methods for extracting mRNA from a biological sample. The general methods of mRNA preparation can be followed, see, e.g., Sambrook and Russell, supra; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Ws.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of DNA or mRNA Level

Once DNA or mRNA is extracted from a sample, the amount of human NAMPT genomic DNA or mRNA may be quantified. The preferred method for determining the DNA or mRNA level is an amplification-based method, e.g., by polymerase chain reaction (PCR), especially reverse transcription-polymerase chain reaction (RT-PCR) for mRNA quantitative analysis.

While NAMPT genomic DNA is directly subject to amplification, mRNA must be first reverse transcribed. Prior to the amplification step, a DNA copy (cDNA) of the human NAMPT mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Sam-Romero and Rotbart in *Diagnostic Molecular Biology: Principles and Applications* pp. 401-406, Persing et al., eds., Mayo Foundation, Rochester, Minn. (1993); Egger et al., *J Clin Microbiol* 33:1442-1447, (1995); and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target genomic DNA or mRNA is typically used in practicing the present disclosure, one of skill in the art will recognize, however, that amplification of these DNA or mRNA species in a sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of DNA or mRNA in the sample. For a review of branched-DNA signal amplification for direct quantitation of nucleic acid sequences in clinical samples, see Nolte, *Adv Clin Chem* 33:201-235 (1998).

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present disclosure. PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

Following any amplification or step such as primer extension, it may be desirable to separate the amplification or primer extension product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as H PLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant disclosure are described in U.S. Pat. Nos. 5,840,873, 5,843,640, 5,843,651, 5,846,708, 5,846,717, 5,846,726, 5,846,729, 5,849.487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Reverse transcription (RT) of RNA to cDNA followed by relative quantitative PCR (RT-PCR) can be used to determine the relative concentrations of specific mRNA species isolated from a cell, such as a NAMPT-encoding transcript. By determining that the concentration of a specific mRNA species varies, it is shown that the gene encoding the specific mRNA species is differentially expressed.

Specifically contemplated are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al., 1991). It is contemplated that this technology may be used in conjunction with evaluating the expression level of NAMPT with respect to diagnostic methods of the present disclosure.

2. Other Quantitative Methods

The NAMPT DNA or mRNA can also be detected using other standard techniques, well known to those of skill in the art. Although the detection step is typically preceded by an amplification step, amplification is not required in the methods of the invention. For instance, the DNA or mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target DNA or mRNA, the amount of which may then be compared to the control based on the intensity of the band. Alternatively, oligonucleotide probes specific to NAMPT DNA or mRNA can be used to detect the presence of such DNA or mRNA species and indicate the amount of DNA or mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, In situ Hybridization, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, $^{99m}$Tc, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Polynucleotides and oligonucleotides (e.g., oligonucleotides complimentary to NAMPT polynucleotide or oligonucleotide) used as probes and primers may be chemically synthesized according to the solid phase phosphoramidite triester method first described by Beaucage and Caruthers, *Tetrahedron Letts*, 22:1859-1862, 1981, using an automated synthesizer, as described in Needham-VanDevanter et al., *Nucleic Acids Res* 12:6159-6168, 1984. Purification of oligonucleotides is by either native acrylamide gel electrophoresis or by anion-exchange HPLC as described in Pearson and Regnier, *J Chrom*, 255:137-149, 1983.

In some embodiments of the invention, NAMPT expression is evaluated by assessing NAMPT transcription. NAMPT transcription can be assessed by a variety of methods including those that involve amplifying NAMPT transcripts or performing Northern blotting on NAMPT transcripts. Amplification of NAMPT transcripts can be utilized in quantitative polymerase chain reactions, which are well known to those of ordinary skill in the art. Alternatively, nuclease protection assays may be implemented to quantify NAMPT transcripts. Other methods that take advantage of hybridization between a probe and target are also contemplated for assessing NAMPT transcription, such as fluorescence in situ hybridization (FISH), or RNA in situ hybridization (RISH). In another embodiment, RNA expression of NAMPT is measured using microarrays which can be manufactured containing either global genomic sequence content or disease-specific biomarkers.

C. Polynucleotides and Oligonucleotides for NAMPT Detection

Described herein are polynucleotides and oligonucleotides that are capable of detecting NAMPT expression. The polynucleotides or oligonucleotides described herein may be complementary to all or part of a nucleic acid sequence encoding NAMPT (e.g., SEQ ID NO: 1). These nucleic acids may be used directly or indirectly to assess, evaluate, quantify, or determine NAMPT expression.

A nucleic acid sequence complementary to all or part of a NAMPT sequence is contemplated for use with the methods described herein. In certain embodiments, there is a nucleic acid that is complementary to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500,7000, 7500, 8000, 8500, 9000, 9500, 10000, or more contiguous nucleotides, nucleosides, or base pairs (or any range derivable therein), including such sequences from SEQ ID NO: 1.

The various probes and primers designed around the nucleotide sequences described herein may be of any length, such as described above. By assigning numeric values to a sequence, for example, the first residue is 1, the second residue is 2, etc., an algorithm defining all primers can be proposed: n to n+y, where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The use of a probe or primer of between 13 and 100 nucleotides, preferably between 17 and 100 nucleotides in length, or in some aspects, up to 1-2 kilobases or more in length, allows the formation of a duplex molecule that is both stable and selective. Such probes or primers can be complementary to lengths, as described above, of SEQ ID NO: 1. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Probes may be complementary (also referred to as "complementarity") to at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, of sequences disclosed herein. In some embodiments, the sequence is SEQ ID NO: 1.

Alternatively, probes may be complementary (also referred to as "complementarity") to at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, of sequences disclosed herein. In some embodiments, the sequence is SEQ ID NO: 1

Accordingly, the nucleotide sequences described herein may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes (e.g., NAMPT gene) or for detecting specific mRNA (e.g., NAMPT mRNA) transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences described herein in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR, for detection of expression of NAMPT, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present disclosure are disclosed in U.S. Pat. Nos. 5,849,481, 5,849,486 and 5,851,772. The relevant portions of these and other references identified in this section of the Specification are incorporated herein by reference.

Nucleic acids used as a template for amplification (e.g., nucleic acids used as a template for amplification of NAMPT) may be isolated from cells, tissues, plasma, or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

III. Quantitation of Polypeptides

A. Obtaining Samples

The present disclosure relates to a method (e.g., in vitro method) of measuring the amount of NAMPT protein found in a cell, tissue (e.g., lung tissue, tonsillar tissue, thoracic tissue, etc.) or plasma sample of a subject, as a means to detect the presence, to assess the risk of developing, to diagnose, to prognose, and/or to monitor the progression or treatment efficacy of RILI. Thus, the first steps of practicing the methods of this disclosure (e.g., e.g., in vitro methods to use NAMPT as a biomarker for diagnosis, prognosis, and/or monitoring of RILI) are to obtain a cell, tissue or plasma sample from a test subject and extract protein from the sample.

A. Acquisition and Preparation of Samples

A biological sample (e.g., cell, tissue (e.g., lung tissue, tonsillar tissue, thoracic tissue, etc.) or plasma) is obtained from a person to be tested or monitored for RILI using a method of the present disclosure. Biological samples of the same type should be taken from both a test subject (e.g., a subject suspected to have RILI and/or a subject at a risk of developing RILI) and a control subject (e.g., a subject not suffering from RILI and/or any lung disorder). Collection of a biological sample from a subject, such as a test subject is performed in accordance with the standard protocol hospitals or clinics generally follow. An appropriate amount of biological sample (e.g., cell, tissue (e.g., lung tissue, tonsillar tissue, thoracic tissue, etc.) or plasma) is collected and may be stored according to standard procedures prior to further preparation.

The analysis of NAMPT protein found in biological sample of a subject (e.g., test subject) according to the method disclosed herein may be performed using, e.g., cells, tissues, or plasma. The methods for preparing biological samples for protein extraction are well known among those of skill in the art. For example, tissue of a subject (e.g., test subject) should be first treated to disrupt cellular membrane so as to release protein contained within the cells.

For the purpose of detecting the presence of RILI or assessing the risk of developing RILI in a test subject, a biological sample may be collected from the subject and the level of human NAMPT protein may be measured and then compared to the normal level of NAMPT protein (e.g., compared to the level of NAMPT protein in same type of biological sample in the subject before the onset of RILI and/or compared to the level of NAMPT protein in same type of biological sample from a control subject). If an increase in the level of human NAMPT protein is observed when compared to the normal level of NAMPT, the test subject is deemed to have RILI or have an elevated risk of developing RILI. For the purpose of monitoring disease progression or assessing therapeutic effectiveness in RILI patients, biological sample from an individual patient may be taken at different time points, such that the level of human NAMPT protein can be measured to provide information indicating the state of disease. For instance, when a patient's NAMPT protein level shows a general trend of decrease over time, the patient is deemed to be improving in the severity of RILI or the therapy the patient has been receiving is deemed effective. A lack of change in a patient's NAMPT protein level or a continuing trend of increase on other hand would indicate a worsening of the condition and ineffectiveness of the therapy given to the patient. Generally, a higher NAMPT protein level seen in a patient indicates a more severe form of RILI the patient is suffering from and a worse prognosis of the disease.

B. Preparing Samples for NAMPT Protein Detection

Tissue or plasma sample from a subject is suitable for the present invention and can be obtained by well-known methods and as described in the previous section. In certain applications of this invention, lung tissue may be the preferred sample type.

C. Determining the Level of Human NAMPT Protein

A protein of any particular identity, such as NAMPT protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. One common method of detection is the use of autoradiography by using a radiolabeled detection agent (e.g., a radiolabeled anti-NAMPT antibody) that is labeled with radioisotopes (e.g., $^3$H, $^{125}$I, $^{35}$S, $^{14}$C, or $^{32}$P, $^{99m}$Tc, or the like). The choice of radioactive isotope depends on research preferences due to ease of synthesis, stability, and half-lives of the selected isotopes. Other labels that can be used for labeling of detection agents (e.g., for labeling of anti-NAMPT antibody) include compounds (e.g., biotin and digoxigenin), which bind to anti-ligands or antibodies labeled with fluorophores, chemiluminescent agents, fluorophores, and enzymes (e.g., HRP). Such immunological assays can be carried out using microfluidic devices such as microarray protein chips. A protein of interest (e.g., human NAMPT protein) can also be detected by gel electrophoresis (such as 2-dimensional gel electrophoresis) and western blot analysis using specific antibodies. In some embodiments, standard ELISA techniques can be used to detect a given protein (e.g., human NAMPT protein), using the appropriate antibodies. In other embodiments, standard western blot analysis techniques can be used to detect a given protein (e.g., human NAMPT protein), using the appropriate antibodies. Alternatively, standard immunohistochemical (IHC) techniques can be used to detect a given protein (e.g., human NAMPT protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human NAMPT protein) can be generated by known techniques.

In some embodiments, NAMPT protein (e.g., NAMPT protein in a biological sample) can be detected (e.g., can be detected in a detection assay) with an antibody that binds to NAMPT, such as an anti-NAMPT antibody, or an antigen-binding fragment thereof. In certain embodiments, an anti-NAMPT antibody is used as a detection agent, such as a detection antibody that binds to NAMPT and detects NAMPT (e.g., from a biological sample), such as detects NAMPT in a detection assay (e.g., in western blot analysis, immunohistochemistry analysis, autoradiography analysis, and/or ELISA). In certain embodiments, an anti-NAMPT antibody is used as a capture agent that binds to NAMPT and detects NAMPT (e.g., from a biological sample), such as detects NAMPT in a detection assay (e.g., in western blot analysis, immunohistochemistry analysis, autoradiography analysis, and/or ELISA). In some embodiments, an antibody that binds to NAMPT, such as an anti-NAMPT antibody, or an antigen-binding fragment thereof is labeled for ease of detection. In some embodiments, an antibody that binds to NAMPT, such as an anti-NAMPT antibody, or an antigen-binding fragment thereof is radiolabeled (e.g., labeled with a radioisotope, such as labeled with $^3$H, $^{125}$I, $^{35}$S, $^{14}$C, or $^{32}$P, $^{99m}$Tc, or the like), enzymatically labelled (e.g., labeled with an enzyme, such as with horseradish peroxidase (HRP)), fluorescent labeled (e.g., labeled with a fluorophore), labeled with a chemiluminescent agent and/or labeled with a compound (e.g., with biotin and digoxigenin).

Other methods may also be employed for measuring the level of NAMPT protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring (SIM) mode, and the electrospray ionization (ESI) based QTOP mass spectrometer. See, e.g., Pan et al., *J Proteome Res* 2009 February; 8(2):787-797.

In specific aspects, NAMPT expression is evaluated by assessing NAMPT protein. In some embodiments, an anti-NAMPT antibody can be used to assess NAMPT protein. Such methods may involve using IHC, western blot analyses, ELISA, immunoprecipitation, autoradiography, or an antibody array. In particular embodiments, NAMPT protein is assessed using IHC. The use of IHC may allow for quantitation and characterization of NAMPT protein. IHC may also allow an immunoreactive score for the sample in which the expression of NAMPT protein is to be determined. The term "immunoreactive score" (IRS) refers to a number that is calculated based on a scale reflecting the percentage of positive cells (on a scale of 1-4, where 0=0%, 1=<10%, 2=10%-50%, 3=50%-80%, and 4=>80%) multiplied by the intensity of staining (on a scale of 1-3, where 1=weak, 2=moderate, and 3=strong). IRS may range from 0-12.

IV. Establishing a Standard Control

In order to establish a standard control for practicing the method of this invention, a group of healthy persons free of any lung disease (especially any form of lung injury, such as RILI) as conventionally defined is first selected. These individuals are within the appropriate parameters, if applicable, for the purpose of screening for and/or monitoring RILI using the methods of the present invention. Optionally, the individuals are of same gender, similar age, or similar ethnic background.

The healthy status of the selected individuals (e.g., control subjects) is confirmed by well established, routinely employed methods including but not limited to general physical examination of the individuals and general review of their medical history.

Furthermore, the selected group of healthy individuals must be of a reasonable size, such that the average amount/concentration of human NAMPT genomic DNA, NAMPT mRNA, or NAMPT protein in the tissue sample obtained from the group can be reasonably regarded as representative of the normal level of NAMPT or average level of NAMPT among the general population of healthy people. Preferably, the selected group comprises at least 10 human subjects.

Once an average value for the NAMPT genomic DNA, mRNA, or protein is established based on the individual values found in each subject of the selected healthy or control group, this average or median or representative value or profile is considered a standard control or is considered the normal level of NAMPT expression. A standard deviation is also determined during the same process. In some cases, separate standard controls may be established for separately defined groups having distinct characteristics such as age, gender, or ethnic background.

In further embodiments, NAMPT expression is evaluated by assaying the level of NAMPT activity.

Use of NAMPT as a Therapeutic Target in RILI

Disclosed herein are methods and compositions for use of NAMPT as a therapeutic target in RILI. In some embodiments, the present disclosure describes the use of a NAMPT inhibitor for treating RILI. In some embodiments, one or more NAMPT inhibitors is used for treating RILI in a subject exposed to radiation, such as whole thorax lung irradiation (WTLI), total body irradiation (TBI) or partial body irradiation (PBI). In some embodiments, one or more NAMPT inhibitors is used for treating RILI in a subject undergoing radiotherapy (e.g., thoracic radiotherapy), such as in a cancer patient undergoing radiotherapy (e.g., thoracic radiotherapy). In some embodiments, one or more NAMPT inhibitors is used for treating RILI in a subject who underwent radiotherapy (e.g., thoracic radiotherapy), such as in a cancer patient who underwent radiotherapy (e.g., thoracic radiotherapy). In some embodiments, one or more NAMPT inhibitors is used for treating RILI in a subject exposed to radiation (e.g., WTLI, TBI, or PBI), e.g., from a nuclear incident. In some embodiments, one or more NAMPT inhibitors is used for treating RILI in a subject who is diagnosed to have RILI using the diagnostic methods described hereinabove. For example, by the methods described hereinabove, expression of NAMPT can be evaluated in a subject who is exposed to radiation and/or a subject who is at a risk of developing RILI, and once the subject is diagnosed to have RILI, the subject can be treated with one or more NAMPT inhibitors. NAMPT inhibitors, as described herein, may include, without limitations, NAMPT siRNAs, NAMPT ribozymes, NAMPT antibodies, and other NAMPT binding proteins or proteins that inhibit the expression of NAMPT transcripts. In particular, an anti-NAMPT antibody can be used (e.g., as a NAMPT inhibitor) for treating RILI in a subject (e.g., a subject (e.g., cancer patient) undergoing thoracic radiotherapy, or a subject exposed to IR, e.g., from a nuclear incident).

In some embodiments, a NAMPT inhibitor (e.g., an anti-NAMPT antibody, such as, a humanized anti-NAMPT monoclonal antibody), which can be used to treat RILI in a subject, may decrease the expression of NAMPT in one or more tissues (e.g., lung tissue, tonsillar tissue, thoracic tissue, etc.) and/or plasma of the subject. In some embodiments, a NAMPT inhibitor (e.g., an anti-NAMPT antibody, such as, a humanized anti-NAMPT monoclonal antibody), which can be used to treat RILI in a subject, may decrease inflammation (e.g., may decrease the expression of one or more proinflammatory cytokines, such as IL-1, IL-6, IL-12, IL-18, TNF, IFN-gamma, etc.) in one or more tissues (e.g., lung tissue, tonsillar tissue, thoracic tissue, etc.) of the subject. In some embodiments, a NAMPT inhibitor (e.g., an anti-NAMPT antibody, such as, a humanized anti-NAMPT monoclonal antibody), which can be used to treat RILI in a subject, may decrease the activation of NFκB (e.g., may decrease the phosphorylation of NFκB) in one or more tissues (e.g., lung tissue, tonsillar tissue, thoracic tissue, etc.) of the subject. In some embodiments, a NAMPT inhibitor (e.g., an anti-NAMPT antibody, such as, a humanized anti-NAMPT monoclonal antibody), which can be used to treat RILI in a subject, may decrease lung injury in the subject. In some embodiments, a NAMPT inhibitor (e.g., an anti-NAMPT antibody, such as, a humanized anti-NAMPT monoclonal antibody), which can be used to treat RILI in a subject, may decrease lung fibrosis (such as radiation induced lung fibrosis (RILF)) in the subject. In some embodiments, a NAMPT inhibitor (e.g., an anti-NAMPT antibody, such as, a humanized anti-NAMPT monoclonal antibody), which can be used to treat RILI in a subject, may decrease collagen deposition in lung tissue of the subject. In some embodiments, a NAMPT inhibitor (e.g., an anti-NAMPT antibody, such as, a humanized anti-NAMPT monoclonal antibody), which can be used to treat RILI in a subject, may decrease the expression of lung tissue smooth muscle actin (SMA) in the subject. In some embodiments, a NAMPT inhibitor (e.g., an anti-NAMPT antibody, such as, a humanized anti-NAMPT monoclonal antibody), which can be used to treat RILI in a subject, may decrease myofibroblast transition and/or fibrosis of lung tissue in the subject.

In some embodiments, a NAMPT inhibitor (e.g., an anti-NAMPT antibody, such as, a humanized anti-NAMPT monoclonal antibody), which can be used to treat RILI in a subject, may be administered to the subject parenterally or orally. In particular, a NAMPT inhibitor (e.g., an anti-NAMPT antibody, such as, a humanized anti-NAMPT monoclonal antibody), which can be used to treat RILI in a subject, may be administered to the subject intravenously.

Nucleic Acids

Disclosed herein are polynucleotides or nucleic acid molecules relating to NAMPT sequences for use in diagnostic, therapeutic, and preventative applications in RILI. In certain embodiments, the present disclosure concerns a nucleic acid that can be used to diagnose RILI based on the detection of over-expression of a NAMPT sequence under stringent or highly stringent hybridization conditions. In other embodiments, the present disclosure specifically concerns a nucleic acid that serves as a NAMPT inhibitor for the prevention or treatment of RILI. Nucleic acids or polynucleotides disclosed herein may be DNA or RNA, and they may be oligonucleotides (100 residues or fewer) in certain embodiments. Moreover, they may be recombinantly produced or synthetically produced. These polynucleotides or nucleic acid molecules may be isolatable and purifiable from cells or they may be synthetically produced. In some embodiments, a NAMPT-encoding nucleic acid is the target of a nucleic acid NAMPT inhibitor, such as a ribozyme or siRNA that reduces the level of NAMPT expression.

The nucleic acid molecule hybridizing to NAMPT may comprise a contiguous nucleic acid sequence that is complementary to the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105,106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147,148, 149, 150, 151, 152, 153, 154, 155, 156, 157, 158, 159, 160, 161,162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310,320, 330, 340, 350, 360, 370, 380,390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more (or any range derivable therein) nucleotides, nucleosides, or base pairs of the NAMPT sequence. Such sequences may be identical or complementary to SEQ ID NO: 1.

Accordingly, sequences that have or have at least or at most about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, of nucleic acids that are complementary to a nucleic acid sequence of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105,106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147,148, 149, 150, 151, 152, 153, 154, 155, 156, 157, 158, 159, 160, 161,162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310,320, 330, 340, 350, 360, 370, 380,390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 contiguous bases (or any range derivable therein) of SEQ ID NO: 1 are contemplated as part of the present disclosure. They may be used as NAMPT inhibitors or as detection probes or primers for use in the methods described herein.

Antisense Sequences, Including siRNAs

In some embodiments, a nucleic acid described herein may encode an anti-sense construct. Antisense methodology takes advantage of the fact that nucleic acids tend to pair with complementary sequences. By complementary, it is meant that polynucleotides are those which are capable of base-pairing according to the standard Watson-Crick complementarity rules. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as, within a host animal, including a human subject.

Antisense constructs may be designed to bind to the promoter and other control regions, exons, introns or even exon-intron boundaries of a gene. It is contemplated that the most effective antisense constructs will include regions complementary to intron-exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

Complementary or antisense polynucleotide sequences are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions. It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

In certain embodiments, the nucleic acid encodes an interfering RNA or siRNA. RNA interference (also referred to as RNA-mediated interference or RNAi) is a mechanism by which gene expression can be reduced or eliminated. Double stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp and Zamore, 2000; Tabara et al., 1999). Activation of these mechanisms targets mature, dsRNA-complementary mRNA for destruction. Advantages of RNAi include a very high specificity, ease of movement across cell membranes, and prolonged down-regulation of the targeted gene. Moreover, dsRNA has been shown to silence genes in a wide range of systems, including plants, protozoans, fungi, C. elegans, Trypanasoma, Drosophila, and mammals. It is generally accepted that RNAi acts post-transcriptionally, targeting RNA transcripts for degradation. It appears that both nuclear and cytoplasmic RNA can be targeted (Bosher and Labouesse, 2000).

siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). The making of siRNAs has been mainly through direct chemical synthesis; or through an in vitro system derived from S2 cells. Chemical synthesis proceeds by making two single stranded RNA-oligomers followed by the annealing of the two single stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTaT to distinguish them from the typical nucleotides incorporated into RNA. The literature has indicated that the use of dT overhangs is primarily motivated by the need to reduce the cost of the chemically synthesized RNAs. It is also suggested that the dTaT overhangs might be more stable than UU overhangs, though the data available shows only a slight (<20%) improvement of the dTdT overhang compared to an siRNA with a UU overhang.

In some embodiments, the present disclosure provides an siRNA that is capable of triggering RNA interference, a process by which a particular RNA sequence is destroyed. siRNA are dsRNA molecules that are 100 bases or fewer in length (or have 100 basepairs or fewer in its complementarity region). In some cases, it has a 2 nucleotide 3' overhang and a 5' phosphate. The particular RNA sequence is targeted as a result of the complementarity between the dsRNA and the particular RNA sequence. It will be understood that dsRNA or siRNA of the present disclosure can effect at least about 15%, 20%, 25%, 30%, 35%, 40%, 45%, 50%, 55%, 60%, 65%, 70%, 75%, 80%, 85%, 90%, 95%, or more reduction of expression of a targeted RNA in a cell. dsRNA described herein (the term "dsRNA" will be understood to include "siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105,106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147,148, 149, 150, 151, 152, 153, 154, 155, 156, 157, 158, 159, 160, 161,162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310,320, 330, 340, 350, 360, 370, 380,390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, to sequences (or their complements) disclosed herein. In some embodiments, the sequence is SEQ ID NO: 1. In some embodiments, long dsRNA are employed in which "long" refers to dsRNA that are 1000 bases or longer (or 1000 basepairs or longer in complementarity region). The term "dsRNA" includes "long dsRNA" and "intermediate dsRNA" unless otherwise indicated. In some embodiments, dsRNA can exclude the use of siRNA, long dsRNA, and/or "intermediate" dsRNA (lengths of 100 to 1000 bases or basepairs in complementarity region). It is specifically contemplated that a dsRNA may be a molecule with two separate RNA strands in which one strand has at least one region complementary to a region on the other strand. Alternatively, a dsRNA includes a molecule that is single stranded, yet has at least one complementarity region as described above (see, Sui et al., 2002 and Brummelkamp et al., 2002), in which a single strand with a hairpin loop is used as a dsRNA for RNAi. For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the antisense strand and the strand with a sequence identical to the targeted mRNA is referred to as the sense strand. Similarly, with a dsRNA comprising only a single strand, it is contemplated that the antisense region has the sequence complementary to the targeted mRNA, while the sense region has the sequence identical to the targeted mRNA. Furthermore, it will be understood that sense and antisense region, like sense and antisense strands, are complementary (i.e., can specifically hybridize) to each other.

The single RNA strand or two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105,106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147,148, 149, 150, 151, 152, 153, 154, 155, 156, 157, 158, 159, 160, 161,162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310,320, 330, 340, 350, 360, 370, 380,390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 or more (including the full-length of a particular gene's mRNA without the poly-A tail) bases or basepairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more bases on either or both ends (5' and/or 3') or as forming a hairpin loop between the complementarity regions.

In some embodiments, the strand or strands of dsRNA are 100 bases (or basepairs) or less, in which case they may also be referred to as siRNA. In specific embodiments, the strand or strands of the dsRNA are less than 70 bases in length. With respect to those embodiments, the dsRNA strand or strands may be from 5-70, 10-65, 20-60, 30-55, 40-50 bases or base pairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian cell's antiviral response. Thus, a hairpin dsRNA (one strand) may be 70 or fewer bases in length with a complementary region of 30 basepairs or fewer. In some cases, a dsRNA may be processed in the cell into siRNA.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001). PCT publications WO 99/32619 and WO 01/68836 suggest that RNA for use in siRNA may be chemically or enzymatically synthesized. Both of these texts are incorporated herein in their entirety by reference. The contemplated constructs provide templates that produce RNAs that contain nucleotide sequences identical to a portion of the target gene. Typically, the length of identical sequences provided is at least 25 bases, and may be as many as 400 or more bases in length. Longer dsRNAs may be digested to 21-25mer lengths with endogenous nuclease complex that converts long dsRNAS to siRNAs in vivo. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. U.S. Pat. No. 5,795,715 reports the simultaneous transcription of two complementary DNA sequence strands in a single reaction mixture, wherein the two transcripts are immediately hybridized.

Vectors

Also described herein are vectors that are designed, primarily, to transform cells with a therapeutic or preventative NAMPT inhibitor, thus encoding a NAMPT inhibitor nucleic acid sequence under the control of a eukaryotic promoter (i.e., constitutive, inducible, repressible, tissue specific). Also, the vectors may contain a selectable marker, if, for no other reason, to facilitate their manipulation in vitro. However, selectable markers may play an important role in producing recombinant cells.

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

In some embodiments, the promoter for use in the methods described herein is the cytomegalovirus (CMV) immediate early (IE) promoter. This promoter is commercially available from INVITROGEN in the vector pcDNAIII, which can be used in the methods described herein. Other viral promoters, cellular promoters/enhancers and inducible promoters/enhancers may be used in the methods described herein. Additionally, any promoter/enhancer combination (as per the Eukaryotic Promoter Data Base EPDB) could also be used to drive expression of a nucleic acid of interest.

Another signal that may prove useful is a polyadenylation signal. Such signals may be obtained from the human growth hormone (hGH) gene, the bovine growth hormone (BGH) gene, or SV40.

Internal ribosome binding sites (IRES) elements can be used to create multigene, or polycistronic messages. IRES elements are able to bypass the ribosome scanning model of 5-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs described herein are functionally positioned downstream of a promoter element.

Also provided are methods for administering the compositions disclosed herein (e.g., composition containing one or more NAMPT inhibitor) to a subject (e.g., to subject with RILI). Any nucleic acid molecule described herein may be comprised in a vector. One of skill in the art would be well equipped to construct a vector through standard recombinant techniques, which are described in Sambrook et al., 2001 and Ausubel et al., 1996, both incorporated herein by reference. In addition to encoding a modified polypeptide, such as modified gelonin, a vector may encode non-modified polypeptide sequences, such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

Vector is a carrier nucleic acid molecule into which a nucleic acid sequence can be inserted for introduction into a cell where it can be replicated. A nucleic acid sequence can be exogenous, which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). An expression vector is a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

One method for delivery of the recombinant DNA involves the use of an adenovirus expression vector. Adenovirus expression vectors include those constructs containing adenovirus sequences sufficient to (a) support packaging of the construct, and (b) to ultimately express a recombinant gene construct that has been cloned therein. The adenovirus vector may be replication defective, or at least conditionally defective, the nature of the adenovirus vector is not believed to be crucial to the successful practice of the present disclosure. The adenovirus may be of any of the 42 different known serotypes or subgroups A-F. Adenovirus type 5 of subgroup C is the some starting material in order to obtain the conditional replication-defective adenovirus vector for use in the presently disclosed methods. As stated above, the typical vector according to the present disclosure is replication defective and will not have an adenovirus E1 region. Thus, it will be most convenient to introduce the transforming construct at the position from which the E1-coding sequences have been removed. However, the position of insertion of the construct within the adenovirus sequences is not critical to the successful practice of the present disclosure. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

The retroviruses are a group of single-stranded RNA viruses characterized by an ability to convert their RNA to double-stranded DNA in infected cells by a process of reverse-transcription (Coffin, 1990). In order to construct a retroviral vector, a nucleic acid encoding a gene of interest is inserted into the viral genome in the place of certain viral sequences to produce a virus that is replication-defective. In order to produce virions, a packaging cell line containing the gag, pol, and enV genes but without the LTR and packaging components is constructed (Mann et al., 1983). When a recombinant plasmid containing a cDNA, together with the retroviral LTR and packaging sequences is introduced into this cell line (by calcium phosphate precipitation, for example), the packaging sequence allows the RNA transcript of the recombinant plasmid to be packaged into viral particles, which are then secreted into the culture media (Nicolas and Rubenstein, 1988: Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors include adeno-associated virus (AAV) (described in U.S. Pat. Nos. 5,139,941 and 4,797,368, each incorporated herein by reference), vaccinia virus, other poxviruses, lentivirus, Epstein Barr viruses, and picornaviruses.

Protamine Delivery of Nucleic Acids

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference.

Lipid Formulations for Nucleic Acid Delivery

In a further embodiment, a nucleic acid may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with LIPOFECTAMINE (GIBCO BRL).

Advances in lipid formulations have improved the efficiency of gene transfer in vivo (Smyth-Templeton et al., 1997; WO 98/07408). A novel lipid formulation composed of an equimolar ratio of 1.2-bis(oleoyloxy)-3-(trimethyl ammonio) propane (DOTAP) and cholesterol significantly enhances systemic in vivo gene transfer, approximately 150-fold. The DOTAP:cholesterol lipid formulation is said to form a unique structure termed a "sandwich liposome." This formulation is reported to "sandwich" DNA between an invaginated bi-layer or vase structure. Beneficial characteristics of these lipid structures include a positive colloidal stabilization by cholesterol, two dimensional DNA packing and increased serum stability.

In further embodiments, the liposome is further defined as a nanoparticle. A nanoparticle refers to a submicron particle. The submicron particle can be of any size. For example, the nanoparticle may have a diameter of from about 0.1, 1, 10, 100, 300, 500, 700, 1000 nanometers, or greater. The nanoparticles that are administered to a subject may be of more than one size. Any method known to those of ordinary skill in the art can be used to produce nanoparticles. In some embodiments, the nanoparticles are extruded during the production process. Information pertaining to the production of nanoparticles can be found in U.S. Patent App. Pub. No. 20050143336, U.S. Patent App. Pub. No. 20030223938, U.S. Patent App. Pub. No. 2003.0147966, each of which is herein specifically incorporated by reference into this section.

In certain embodiments, an anti-inflammatory agent is administered with the lipid to prevent or reduce inflammation secondary to administration of a lipid:nucleic acid complex. For example, the anti-inflammatory agent may be a non-steroidal anti-inflammatory agent, a salicylate, an anti-rheumatic agent, a steroid, or an immunosuppressive agent.

DOTAP:Chol nanoparticles can be synthesized by any method known to those of ordinary skill in the art. For example, the method can be in accordance with that set forth in Chada et al., 2003, or Templeton et al., 1997, both of which are herein specifically incorporated by reference.

One of ordinary skill in the art would be familiar with use of liposomes or lipid formulation to entrap nucleic acid sequences. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with LIPOFECTAMINE (GIBCO BRL).

Lipid-mediated nucleic acid delivery and expression of foreign DNA in vitro has been very successful (Nicolau and Sene, 1982; Fraley et al., 1979; Nicolau et al., 1987). Wong et al. (1980) emonstrated the feasibility of lipid-mediated delivery and expression of foreign DNA in cultured chick embryo, HeLa and hepatoma cells. Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro and in vivo gene transfer.

The production of lipid formulations often is accomplished by sonication or serial extrusion of liposomal mixtures after (I) reverse phase evaporation, (II) dehydration-rehydration, (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases. The liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1.

A nucleic acid for nonviral delivery may be purified on polyacrylamide gels, cesium chloride centrifugation gradients, column chromatography or by any other means known to one of ordinary skill in the art. In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of bulk of cellular components or in vitro reaction components, and/or the bulk of the total genomic and transcribed nucleic acids of one or more cells. Methods for isolating nucleic acids (e.g., equilibrium density centrifugation, electrophoretic separation, column chromatography) are well known to those of skill in the art.

Proteins and Polypeptides

Also disclosed herein is are NAMPT inhibitors that are polypeptides. In certain embodiments, the NAMPT polypeptide inhibitors are used in the treatment or prevention of RILI. The terms "protein" and "polypeptide" are used interchangeably herein and they both cover what is understood as a "peptide" (a polypeptide molecule having 100 or fewer amino acid residues). In certain embodiments, the NAMPT inhibitor is a protein, polypeptide, or peptide; in particular embodiments, the NAMPT inhibitor is protein or polypeptide that is an antibody.

As will be understood by those of skill in the art, modification and changes may be made in the structure of a polypeptide or peptide NAMPT inhibitor, and still produce a molecule having like or otherwise desirable characteristics. For example, certain amino acids may be substituted for other amino acids or include deletions, additions, or truncations in the protein sequence without appreciable loss of interactive binding capacity with structures. Since it is the interactive capacity and nature of a protein that defines that protein's biological functional activity, certain amino acid sequence substitutions can be made in a protein sequence (or, its underlying DNA coding sequence) and nevertheless obtain a protein with similar inhibitory properties. It is thus contemplated that various changes may be made in the sequence of NAMPT inhibitor polypeptides or peptides (or underlying DNA) without appreciable loss of their biological utility or activity. It is also well understood that where certain residues are shown to be particularly important to the biological or structural properties of a protein or peptide, e.g., residues in the binding site of an antibody, such residues may not generally be exchanged.

Amino acid substitutions are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all a similar size; and that phenylalanine, tryptophan, and tyrosine all have a generally similar shape. Therefore, based upon these considerations, the following subsets are defined herein as biologically functional equivalents: arginine, lysine, and histidine; alanine, glycine, and serine; and phenylalanine, tryptophan, and tyrosine.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, some, and those within ±0.5 are even more particularly preferred. It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1);

alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +2, ±1, or ±0.5 is contemplated. While discussion has focused on functionally equivalent polypeptides arising from amino acid changes, it will be appreciated that these changes may be effected by alteration of the encoding DNA, taking into consideration also that the genetic code is degenerate and that two or more codons may encode the same amino acid.

In Vitro Protein Production

In addition to the purification methods provided in the examples, general procedures for in vitro protein production are discussed. Following transduction with a viral vector according to some embodiments of the present disclosure, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshney, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present disclosure uses autologous B lymphocyte cell lines, which are transfected with a viral vector that expresses an immunogene product, and more specifically, a protein having immunogenic activity. Other examples of mammalian host cell lines include Vero and HeLa cells, other B- and T-cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tha-, hgprt- or aprt-cells, respectively. Also, anti-metabolite resistance can be used as the basis of selection: for dhfr, which confers resistance to pyrimethamine; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent cells.

Antibody Production

Some embodiments of the present disclosure pertain to methods and compositions involving an inhibitor of NAMPT, wherein the inhibitor is an antibody that binds NAMPT.

Any suitable method for generating monoclonal antibodies may be used. For example, a recipient may be immunized with NAMPT or a fragment thereof. Any suitable method of immunization can be used. Such methods can include adjuvants, other immunostimulants, repeated booster immunizations, and the use of one or more immunization routes.

Any suitable source of NAMPT can be used as the immunogen for the generation of the non-human antibody of the compositions and methods disclosed herein. Such forms include, but are not limited whole protein, peptide(s), and epitopes, generated through recombinant, synthetic, chemical or enzymatic degradation means known in the art. Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

EXAMPLES

Described herein are in vitro and in vivo studies to evaluate NAMPT as a biomarker and therapeutic target in RILI. The following examples are included for purpose of illustration only and are not intended to be limiting.

Example 1. Exploring the Role of NAMPT in RILI

Given the important role for inflammatory cascades in RILI, the effects of radiation on expression of NAMPT, which is a TLR4 ligand and a damage-associated molecular pattern protein, was explored. Three groups of C57/B6 mice were used to assess the role of NAMPT in RILI.

The first group consisted of wild type (WT) mice receiving a single dose of thoracic radiation (20 Gy). Mice treated with 0.1 mg/kg LPS served as positive control, while non-irradiated mice served as negative control ("Controls"). Lung tissues were harvested from the mice at specific times over an 18-week period. Amount of bronchoalveolar lavage (BAL) protein and cytokines was measured, cell counts/differentials were obtained, and NAMPT expression was assessed by RT-PCR in the lung tissues. Lung tissues were also subjected to hematoxylin and eosin (H&E) and NAMPT staining. Moreover, blood was collected from the mice to measure plasma NAMPT expression. Results from the corresponding analyses are provided in FIGS. 1, 2, 3A, 3B, 4, 5A, 5B, 6, and 7.

Figure 5B:
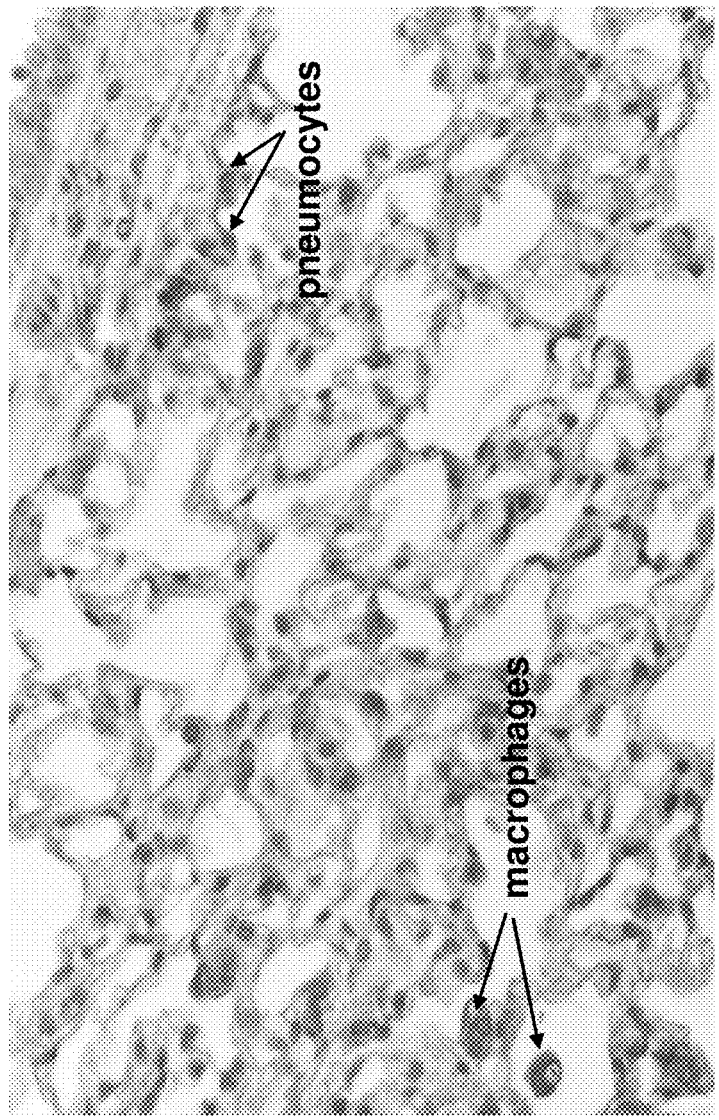
Figure 6:
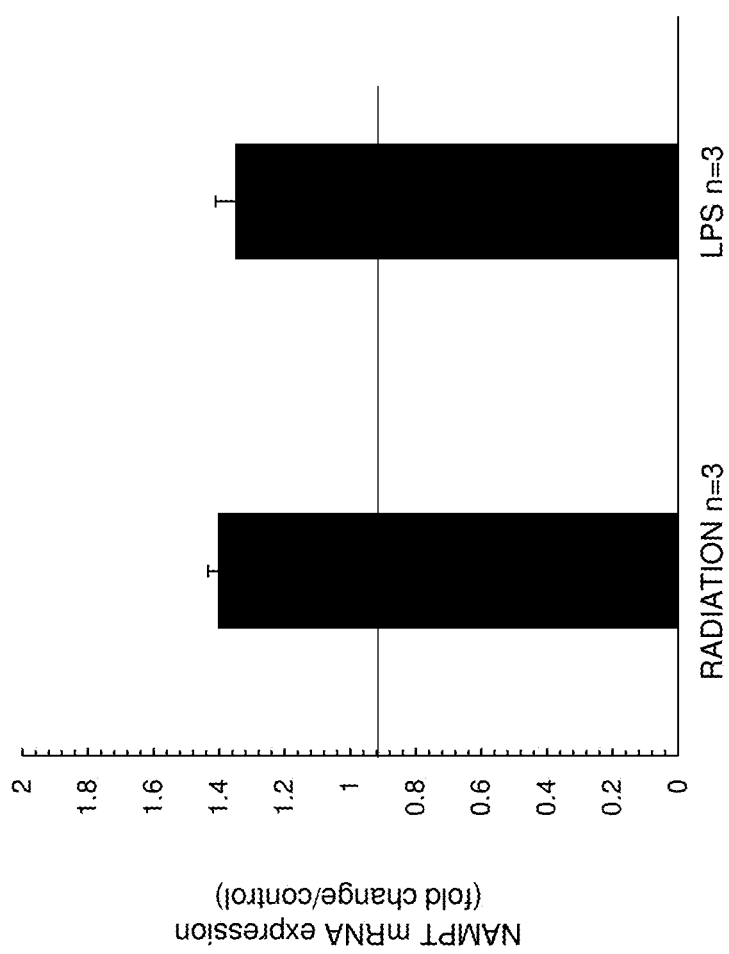
FIG. 6 is a graph depicting fold change in NAMPT mRNA expression in lung tissues of irradiated mice (at 1-week post radiation exposure) over NAMPT mRNA expression in lung tissues of non-irradiated control mice. Also depicted in the graph is fold change of NAMPT mRNA expression in lung tissues from LPS-treated mice over NAMPT mRNA expression in lung tissues from vehicle-treated control mice.
Figure 7:
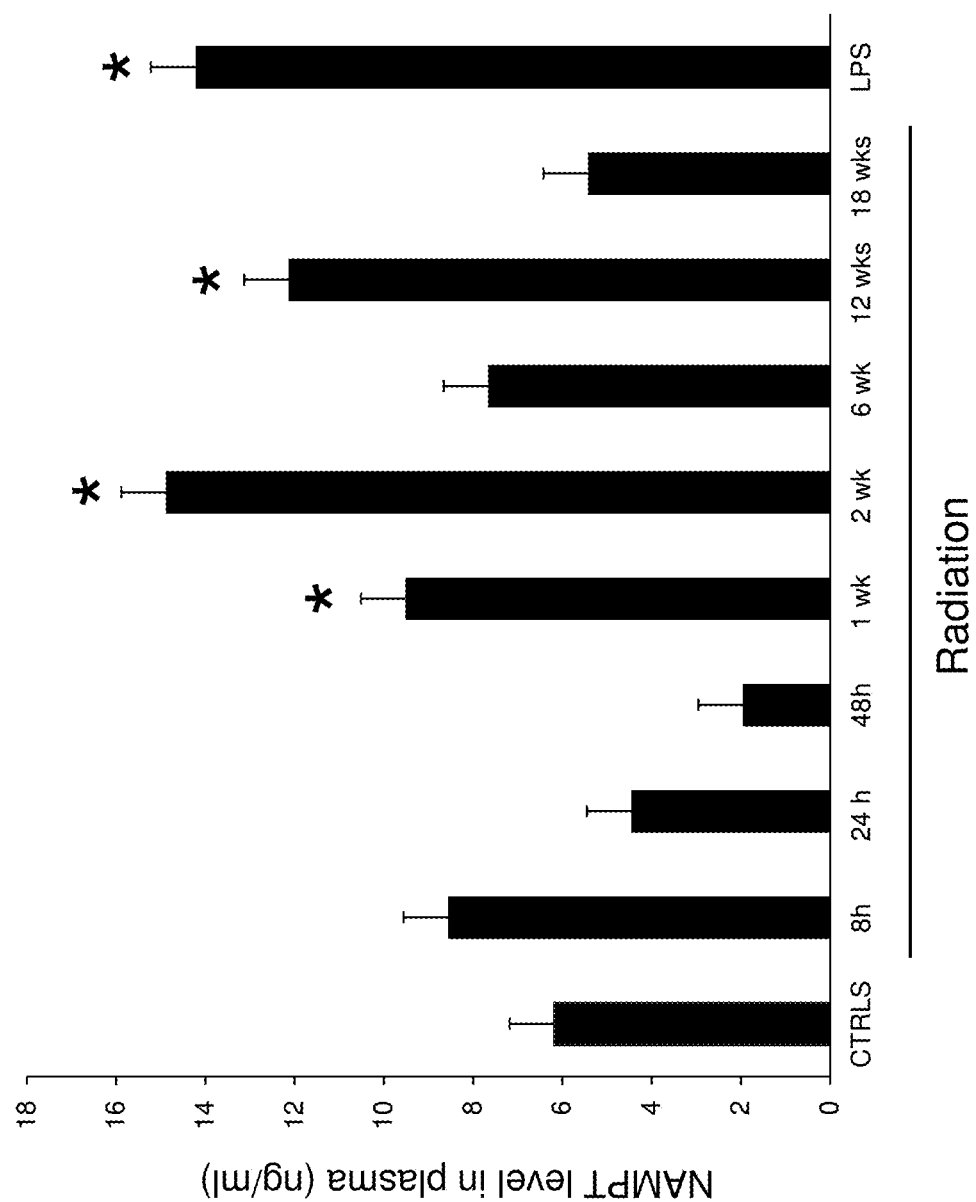
FIG. 7 is a graph depicting the effects of radiation (20 Gy) on the plasma level of NAMPT in mice at 8 hours, 24 hours, 48 hours, 1 week, 2 weeks, 6 weeks, 12 weeks, and 18 weeks post radiation exposure. Also shown in the graph are plasma levels of NAMPT in non-irradiated control mice, and mice that were exposed to 0.1 mg/kg LPS. *indicates $p<0.05$

As described in FIG. 1, compared to control mice, mice that were exposed to radiation displayed significantly increased BAL protein levels (p=0.007) beginning at week 1 post radiation exposure and continuing over the entire 18-week period, with maximum increase observed at week 18 (6-fold). Similarly, as described in FIG. 2, count of BAL-expressing cells (BAL cells) increased significantly (p=0.007) in mice that were exposed to irradiation, with maximum increase observed at week 12 (9-fold). As described in FIGS. 3A and 3B, the increase in BAL cells primarily reflected an increased count of BAL-expressing macrophages (BAL macrophages; p=0.01) (FIG. 3A) and an increased count of BAL-expressing PMNs (BAL PMNs; p=0.005) (FIG. 3B) at weeks 1, 12, and 18, post radiation exposure. Development of RILI in mice at 1-week post radiation exposure was confirmed by H&E staining of lung tissues that displayed acute diffuse alveolar damage compared to lung tissues from non-irradiated controls (FIG. 4). As described in FIGS. 5A and 5B, increased expression of NAMPT was observed in lung tissues from irradiated mice at 1-week post radiation exposure (FIG. 5A, right panel; FIG. 5B) compared to lung tissues from non-irradiated controls (FIG. 5A, left panel). Increased expression of NAMPT in irradiated lung tissues was further confirmed by RT-PCR analysis. As described in FIG. 6, NAMPT mRNA expression was increased in lung tissues at 1-week post radiation exposure (1.4 fold). The increase in NAMPT mRNA expression in irradiated lung tissues persisted through week 12 and declined thereafter (data not shown). Moreover, as described in FIG. 7, 20 Gy radiation increased plasma NAMPT level at as early as 8-hour post radiation exposure; plasma NAMPT level was significantly increased (p<0.05) at 1-week post radiation exposure (1.5 fold), with maximum increase observed at week 2 (2.4 fold).

The second group consisted of NAMPT heterozygous (Nampt$^{+/-}$; "Nampt het") mice that received 20 Gy thoracic radiation and were observed for 4 weeks. Non-irradiated WT and NAMPT heterozygous mice, and irradiated WT mice were used as controls. Lung tissues were harvested from the mice after 4 weeks, and the amount of BAL protein in the lung tissues was measured. Results from the corresponding analyses are provided in FIG. 8.

Figure 8:
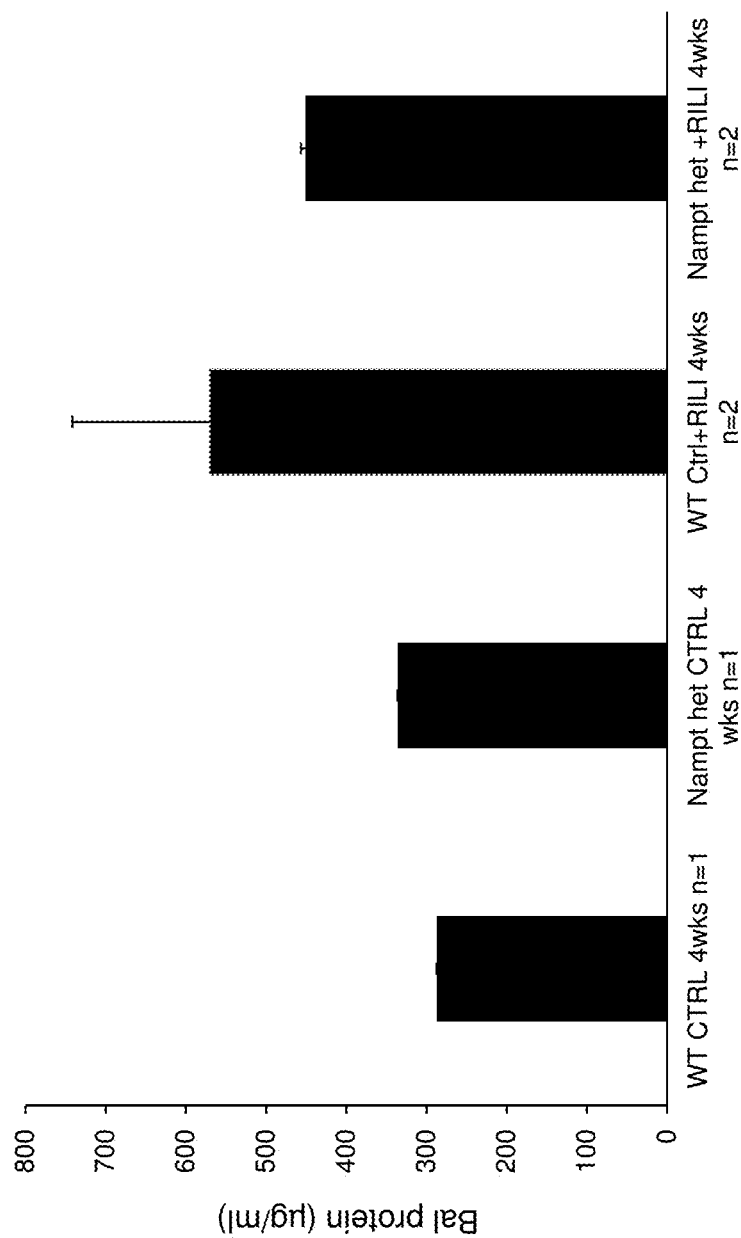
FIG. 8 is a graph depicting the effects of radiation (20 Gy) on the amount of BAL protein in lung tissues of wild-type (WT) and NAMPT heterozygous mice at 4 weeks post radiation exposure. Also shown in the graph are amounts of BAL protein in lung tissues of non-irradiated WT mice and non-irradiated NAMPT heterozygous mice.

As described in FIG. 8, BAL protein was significantly increased in WT mice compared to non-irradiated control at 4-week post radiation exposure. However, NAMPT (+/−) mice demonstrated reduced RILI (BAL indices, H&E staining) at 4 weeks with significant reduction (~20% reduction) in BAL protein level compared to the irradiated WT control, but with no observed change in total BAL cell count.

The third group consisted of radiated mice that received 20 Gy thoracic radiation and were injected intraperitoneally with a polyclonal NAMPT-neutralizing antibody (pAb) (3×/week) or with PBS ("Vehicle"). Lung tissues were harvested from the mice after 4 weeks. Amount of BAL protein was measured, cell counts/differentials were obtained, and NAMPT expression was assessed by RT-PCR in the lung tissues. Moreover, blood was collected from the mice to measure plasma NAMPT expression. Results from the corresponding analyses are provided in FIGS. 9-13.

Figure 9:
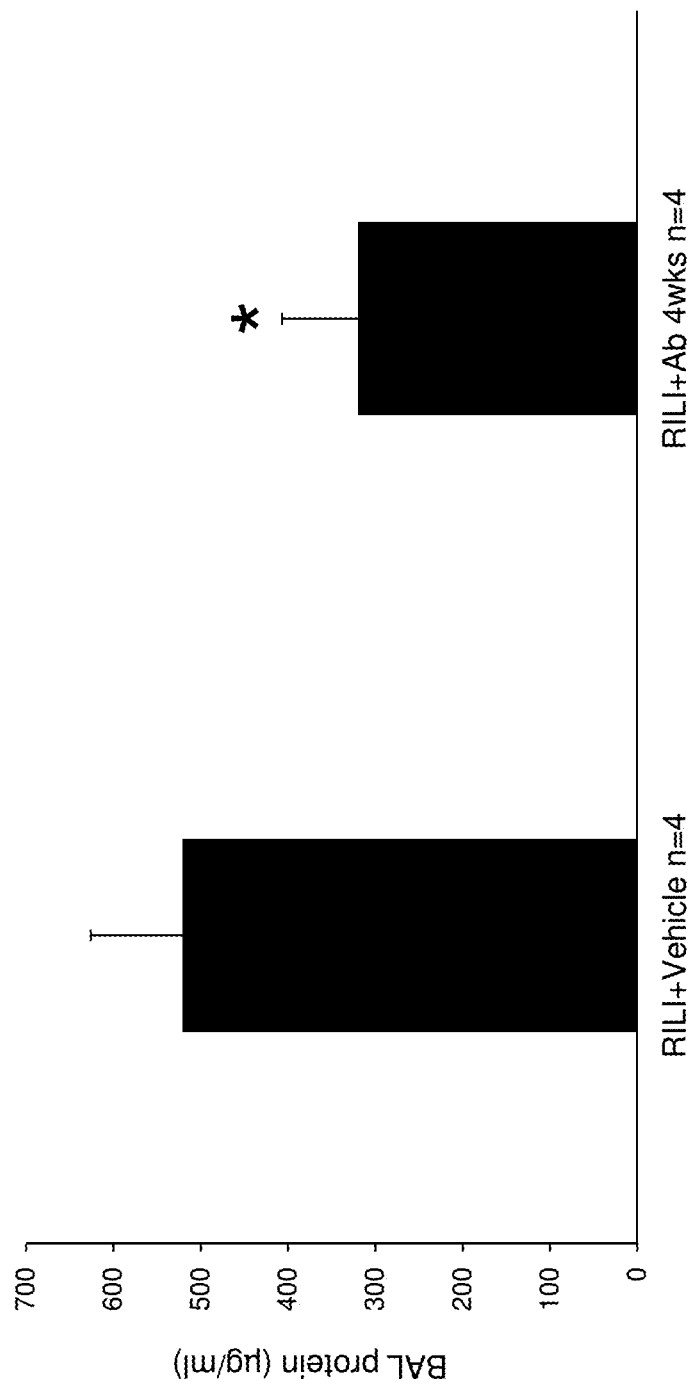
FIG. 9 is a graph depicting the amount of BAL protein in lung tissues of mice that received 20 Gy thoracic radiation and were treated with either a polyclonal NAMPT-neutralizing antibody or a vehicle. The graph shows the amount of BAL protein in the indicated mice at 4 weeks post radiation exposure. * indicates $p<0.05$
Figure 10:
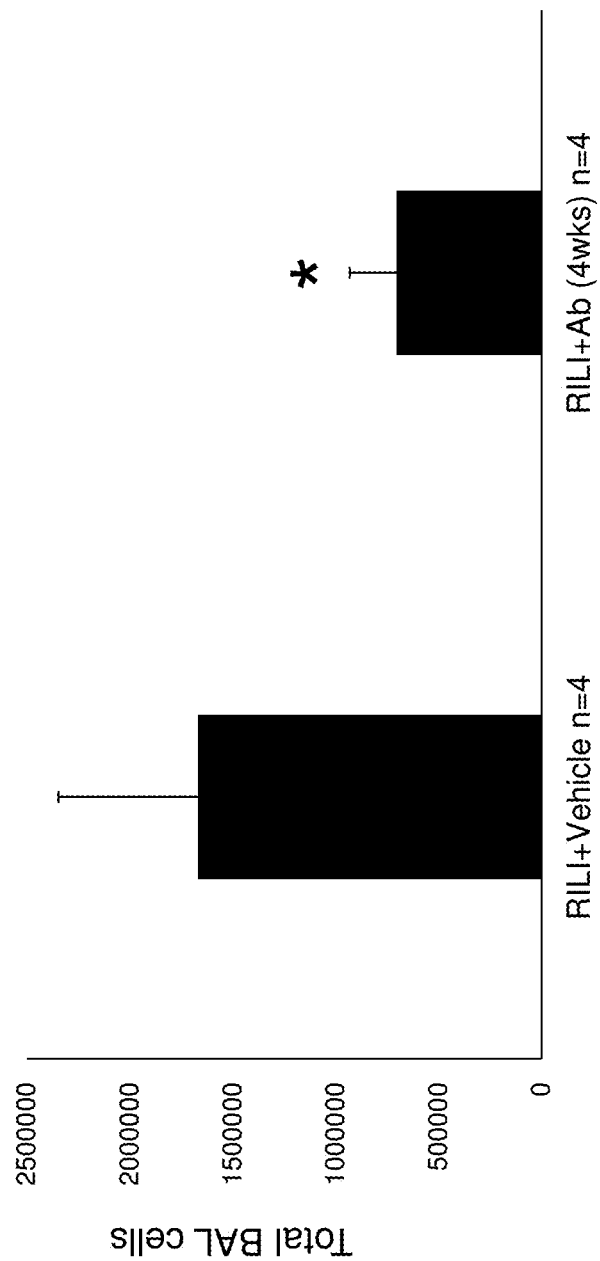
FIG. 10 is a graph depicting the count of BAL cells in lung tissues of mice that received 20 Gy thoracic radiation and were treated with either a polyclonal NAMPT-neutralizing antibody or a vehicle. The graph shows the count of BAL cells in the indicated mice at 4 weeks post radiation exposure. * indicates $p<0.05$
Figure 11:
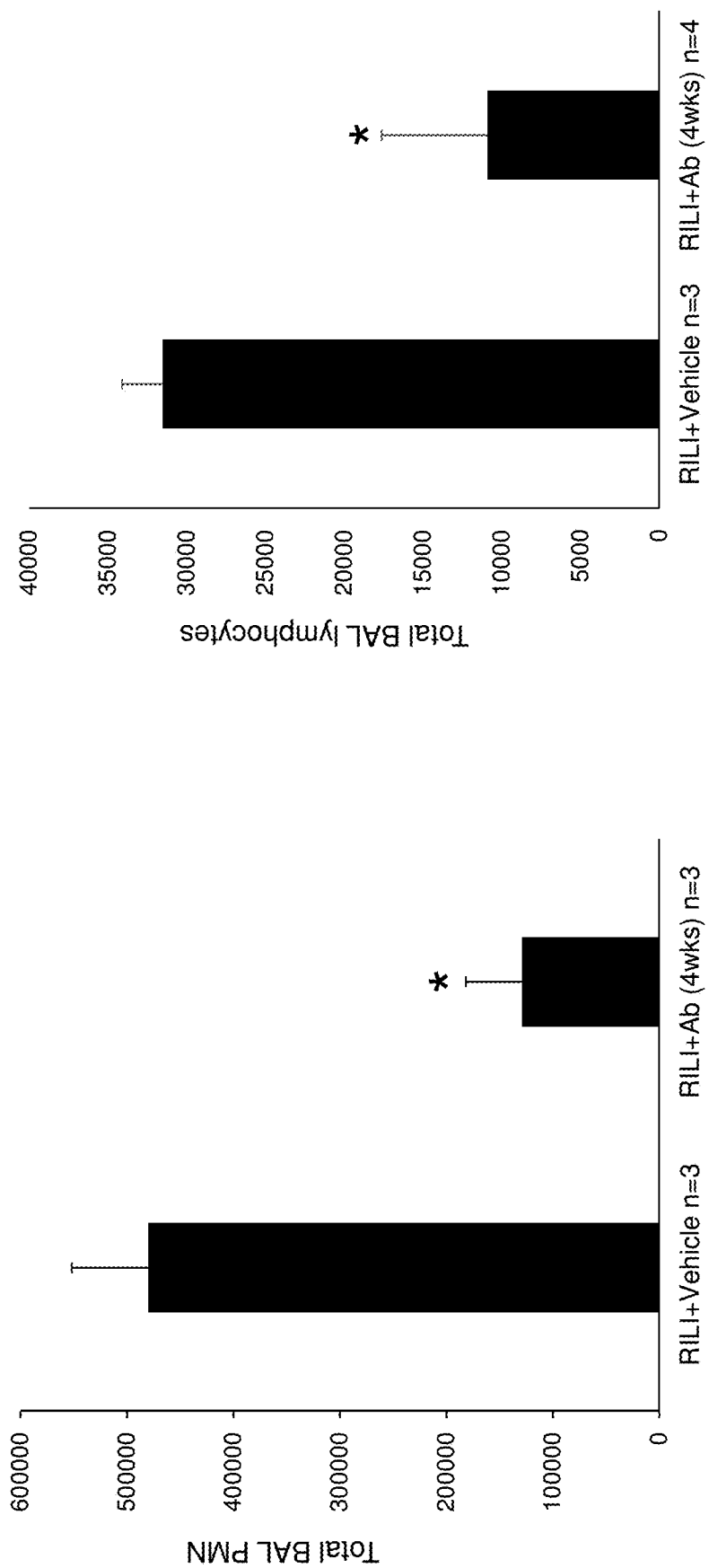
FIG. 11 is a graphical depiction of the count of BAL PMNs and BAL-expressing lymphocytes (BAL lymphocytes) in lung tissues of mice that received 20 Gy thoracic radiation and were treated with either a polyclonal NAMPT-neutralizing antibody or a vehicle. The graph on the left panel shows the count of BAL PMNs, and the graph on the right panel shows the count of BAL lymphocytes in the indicated mice at 4 weeks post radiation exposure. * indicates $p<0.05$
Figure 12:
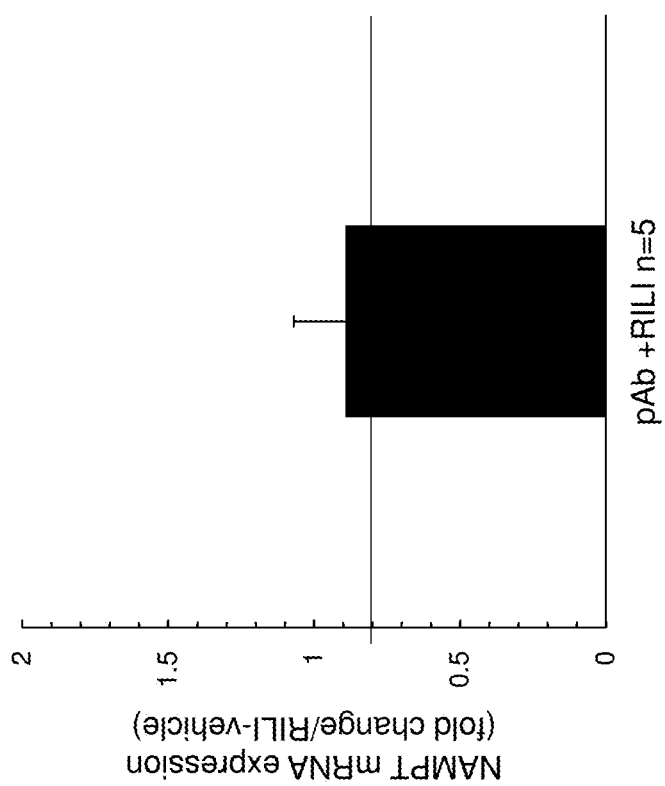
FIG. 12 is a graph depicting fold change in NAMPT mRNA expression in lung tissues of irradiated mice that were treated with a polyclonal NAMPT-neutralizing antibody over NAMPT mRNA expression in lung tissues of irradiated mice that were treated with a vehicle control.
Figure 13:
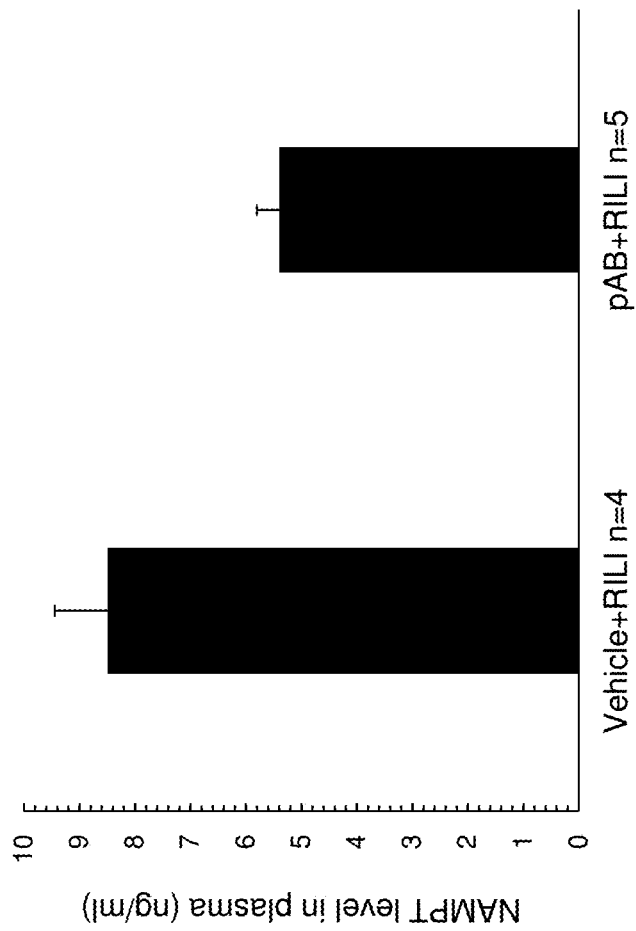
FIG. 13 is a graph depicting plasma levels of NAMPT in irradiated mice that were treated with either a polyclonal NAMPT-neutralizing antibody or a vehicle control.
Figures 16A, 16B:
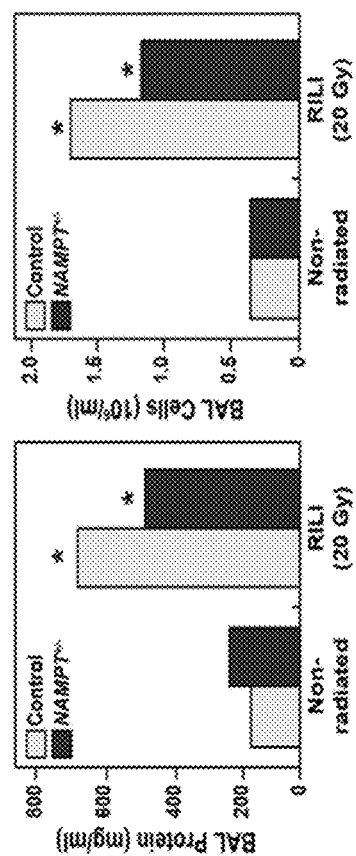
FIGS. 16A-16B are graphical depictions of the amount of BAL protein and count of BAL cells in lung tissue of WT mice ("Control") or NAMPT heterozygous mice (Nampt$^{+/-}$) that were either non-irradiated ("Non-radiated"), or exposed to 20 Gy WTLI ("RILI").

As described in FIGS. 9 and 10, mice treated with the NAMPT-neutralizing pAb demonstrated reduced RILI at 4 weeks compared to vehicle-treated irradiated mice with 40%-60% reduction in BAL protein level (FIG. 9) and total BAL cells (FIG. 10). The decrease in BAL cells following treatment with NAMPT-neutralizing pAb primarily reflected decreased count of BAL PMNs (FIG. 11, left panel) and decreased count of BAL-expressing lymphocytes (BAL-lymphocytes; FIG. 11, right panel) at 4-week post radiation exposure, Moreover, as described in FIG. 12, a 11% decrease in NAMPT mRNA expression level was observed in lung tissues from irradiated mice that were treated with the NAMPT-neutralizing pAb compared to vehicle-treated control. Also, as described in FIG. 13, the level of NAMPT in plasma was reduced by ~36% in irradiated mice that were treated with the NAMPT-neutralizing pAb compared to vehicle-treated control.

Thus, the results outlined in FIGS. 1, 2, 3A, 3B, 4, 5A, 5B, and 6-13 clearly demonstrate a dysregulation of NAMPT expression and secretion in RILI. These findings indicate that NAMPT is a novel biomarker and therapeutic target in RILI that contributes to the pathobiology of radiation-induced injury in lung tissues.

Example 2. Effect of Radiation on NAMPT Expression in Human Tissues and Blood

To further explore the role of NAMPT in RILI, the effects of radiation on expression of NAMPT in human tissues and blood was explored. The results are described in FIGS. 14A-14D.

To assess the effect of radiation on NAMPT expression, human tonsillar epithelial tissue was exposed to 8 Gy ionizing radiation (IR) for 24 hours. As described in FIG. 14A, NAMPT expression in human tonsillar tissues was rapidly and markedly upregulated after 8 Gy IR exposure. The effect of radiation on NAMPT expression was further assessed by studying NAMPT expression in cancer patients undergoing radiotherapy. As described in FIG. 14B, subjects undergoing radiotherapy for breast cancer (n=50) or lung cancer (n=34) exhibited significantly increased plasma level of NAMPT compared to control subjects (n=268) (p<0.0001). The effect of radiation on NAMPT expression was also assessed by studying NAMPT expression in patients with radiation pneumonitis. These subjects were receiving radiotherapy for lung or esophageal cancer with RILI onset an average 6 weeks after initiation of radiotherapy. As described in FIG. 14C, patients with radiation pneumonitis (n=19) exhibited NAMPT plasma level that was 4-5 fold higher than control subjects (n=70) (p<0.001). The effect of radiation on NAMPT expression was further assessed by studying NAMPT expression in patients with acute respiratory distress syndrome (ARDS). As described in FIG. 14D, patients with ARDS (n=338) exhibited NAMPT plasma level that was 4-5 fold higher than control subjects (n=245).

Thus, the results outlined in FIGS. 14A-14D clearly indicate a dysregulation of NAMPT expression and secretion in human RILI.

Example 3. Assessing the Role of NAMPT in RILI Using an In Vivo Model of Radiation Pneumonitis In order to further assess the role of NAMPT in RILI, WT C57/B6 mice and NAMPT heterozygous mice (Nampt$^{+/-}$) were exposed to 20 Gy whole thorax lung irradiation (WTLI) and evaluated at specified time points over an 18-week period. The results are described in FIGS. 15A-15D and FIGS. 16A-16B.

As described in FIGS. 15A-15C, WTLI-exposed WT mice exhibited increased NAMPT expression, especially in alveolar macrophages and epithelial cells, and an increase in inflammation, vascular leakage and inflammatory lung injury 4 weeks (FIG. 15A), 12 weeks (FIG. 15B) and 18 weeks (FIG. 15C) after 20 Gy WTLI compared to sham-exposed mice (non-irradiated mice; shown in inset). FIG. 15D summarizes NAMPT staining in lung tissues 4 weeks, 12 weeks and 18 weeks after IR exposure; sham-exposed mice (non-irradiated mice) served as negative control. On the other hand, NAMPT heterozygous mice (Nampt$^{+/-}$) showed reduced inflammatory lung injury compared to WT mice, as reflected by reduced BAL protein level (FIG. 16A) and count of BAL cells (FIG. 16B) in NAMPT heterozygous mice 4 weeks after 20 Gy WTLI exposure.

Thus, the results described in FIGS. 15A-15D and FIGS. 16A-16B underscore a key role for NAMPT in RILI pathogenesis and indicate the potentials of using NAMPT as a biomarker of RILI.

Example 4. Validating NAMPT as a Therapeutic Target in RILI Using an In Vivo Model of Radiation Pneumonitis To validate NAMPT as a therapeutic target in RILI, WT 057/B6 mice and NAMPT heterozygous mice (Nampt$^{+/-}$) were exposed to 20 Gy WTLI (RILI mice) or sham-IR (non-radiated mice), as described in Example 3. The WT mice were intraperitoneally injected 3×/week with 50 µg of an anti-NAMPT pAb or vehicle control. The mice were evaluated for lung injury and inflammation, BAL protein level, count of BAL cells and plasma NAMPT level after 4 weeks of IR exposure. The results are described in FIGS. 17A-17E.

Compared to sham-IR exposed mice (shown in inset), H&E staining of lung tissues from WTLI-exposed WT mice showed marked increase in lung injury and inflammation (FIG. 17A). In contrast, NAMPT heterozygous mice exposed to 20 Gy IR showed significantly reduced injury (FIG. 17B). Significantly reduced lung injury was also observed in mice that were injected with the anti-NAMPT pAb (FIG. 17C). Decrease in IR-induced injury upon treatment with anti-NAMPT antibody was also reflected by reduced BAL protein level (FIG. 17D, left panel) and count of BAL cells (FIG. 17D, right panel) in mice that were injected with the anti-NAMPT pAb. The anti-NAMPT antibody also decreased NAMPT levels in blood from IR-exposed mice after 4 weeks of IR exposure (FIG. 17E).

Thus, the results described in FIGS. 17A-17E underscore the role of an anti-NAMPT antibody in ameliorating WTLI-induced radiation pneumonitis and lung injury, and validate NAMPT as a therapeutic target in RILI.

Example 5. Validating NAMPT as a Therapeutic Target in RILI Using an In Vivo Model of Radiation-Induced Lung Fibrosis To further validate NAMPT as a therapeutic target in RILI, WT C57/B6 mice and NAMPT heterozygous mice (Nampt$^{+/-}$) were exposed to 20 Gy WTLI, as described in Example 3. The WT mice were intraperitoneally injected 3×/week with 50 µg of an anti-NAMPT pAb or vehicle control, as described in Example 4. The mice were evaluated for radiation-induced lung fibrosis (RILF) by assessing inflammation, collagen deposition, and expression of lung tissue smooth muscle actin (SMA), which is a reflection of myofibroblast transition and fibrosis. The results are described in FIGS. 18A-18E.

Figures 18A, 18B, 18C, 18D, 18E:
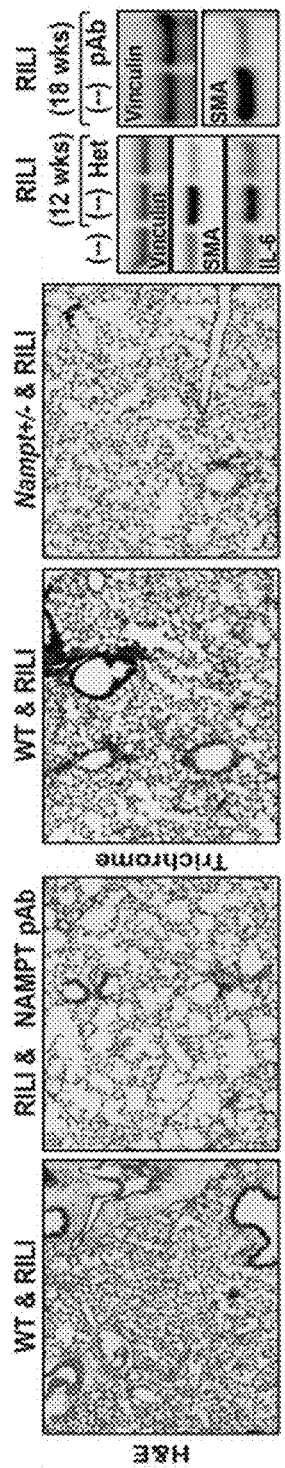
FIGS. 18A-18E are graphical depictions of inflammation, collagen deposition, and expression of smooth muscle actin (SMA) and IL-6 in lung tissue of WT mice that were exposed to 20 Gy WTLI, WT mice that were exposed to 20 Gy WTLI and treated with an anti-NAMPT pAb, or NAMPT heterozygous mice (Nampt$^{+/-}$) that were exposed to 20 Gy WTLI.

As described in FIGS. 18A-18E, 20 Gy IR induced RILF at 12 and 18 weeks, which was reflected by increased inflammation (H&E staining of lung tissues, shown in FIG. 18A; and increased expression of IL-6 in western blot analysis, shown in FIG. 18E), increased collagen deposition (detected by Trichrome staining of lung tissues, shown in FIG. 18C), and increased expression of lung tissue SMA (detected by western blot analyses, shown in FIG. 18E). The anti-NAMPT pAb significantly reduced IR-induced injury at 12 and 18 weeks, which was reflected by decreased inflammation (H&E staining of lung tissues, shown in FIG. 18B), and decreased expression of lung tissue SMA (western blot analyses, shown in FIG. 18E). Similarly, the protective effects of the Nampt$^{+/-}$ genotype was observed with reduced Trichrome staining (18 weeks) (FIG. 18D), as well as reduced levels of SMA and IL-6 in lung tissues 12 weeks after IR exposure (western blot analyses, shown in FIG. 18E).

Thus, the results described in FIGS. 18A-18E underscore the role of an anti-NAMPT Ab and a heterozygous Nampt$^{+/-}$ genotype in attenuating RILF, and further validate NAMPT as a therapeutic target in RILI.

Example 6. Development of a Humanized Anti-NAMPT Antibody Platform for Reducing Systemic Inflammatory Injury In a quest to dampen the activation of evolutionarily-conserved inflammatory pathways, we developed humanized anti-NAMPT antibodies. Following several rounds of subcloning, a panel of anti-NAMPT murine monoclonal antibodies (mAbs) were generated that were highly efficacious in significantly reducing NAMPT-induced NFκB phosphorylation and attenuating murine inflammatory lung injury. Two of these high-affinity murine anti-NAMPT mAbs (AL303, AL310), with Kd of 6 and 9 nM, were selected for humanization. Comprehensive in vitro and in vivo screening of 50 humanized mAbs (25 derived from each murine mAb) utilizing human endothelial cells, and both mouse and rat preclinical models of inflammatory injury, resulted in selection of our lead humanized anti-NAMPT antibodies. Ability of humanized anti-NAMPT antibodies to treat lung injury was tested in vivo, using two murine lung injury models: a "one hit" model of lung injury that was developed by intratracheal delivery of LPS into mice, and a "two hit" model of lung injury that was developed by exposing mice to LPS and mechanical VILI. Either of the humanized anti-NAMPT antibodies was administered to these mice in order to assess the capacity of the antibodies to attenuate acute inflammation and injury. Results from the testing is provided in FIGS. 19A-19C.

Figure 19A:
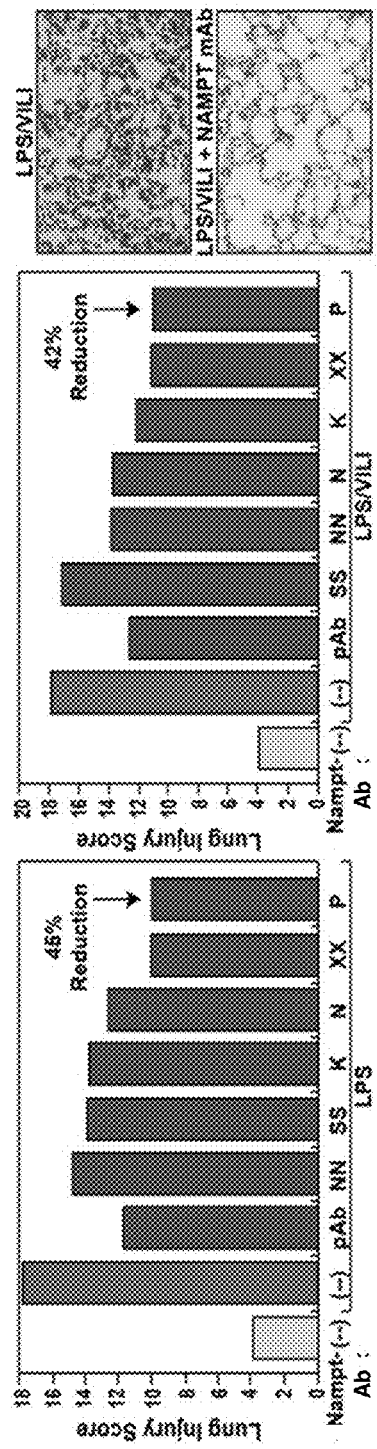
FIGS. 19A-19C depict results from in vivo testing of humanized anti-NAMPT antibodies (NN, SS, K, N, XX, P, and UU) on inflammation and injury in murine lung injury models.

As depicted in FIG. 19A, analysis of integrated lung injury score showed that all of the tested humanized anti-NAMPT antibodies were effective in reducing lung injury in the LPS-induced "one hit" model. However, the most substantial effect was observed with the anti-NAMPT antibody P (45% reduction). As described in FIG. 19B, analysis of integrated lung injury score showed that all of the tested humanized anti-NAMPT antibodies were effective in reducing lung injury in the LPS/VILI-induced "two hit" model. However, the most substantial effect was observed with the anti-NAMPT antibody P (42% reduction). As described in FIG. 19C, anti-NAMPT antibody P was also effective in reducing histologic injury indices in the LPS/VILI-induced "two hit" model of acute inflammatory injury. Accordingly, the humanized anti-NAMPT antibody "P" was selected as a viable RILI therapeutic strategy.

The humanized anti-NAMPT mAb "P" has undergone sequence optimization affecting relevant amino acid substitutions within the VH and VL sequences for improved development, enhanced mAb expression in stable mammalian cell lines and reduced immunogenicity. Sequence alterations were based upon structural and sequential data such as aggregation or post translational modifications (oxidation, deamidation, isomerization), T-cell epitopes, and N-linked glycosylation motifs. Details of development and selection of humanized anti-NAMPT monoclonal antibodies is provided in U.S. Ser. No. 62/883,952, which is incorporated by reference in its entirety.

Figure 19B:
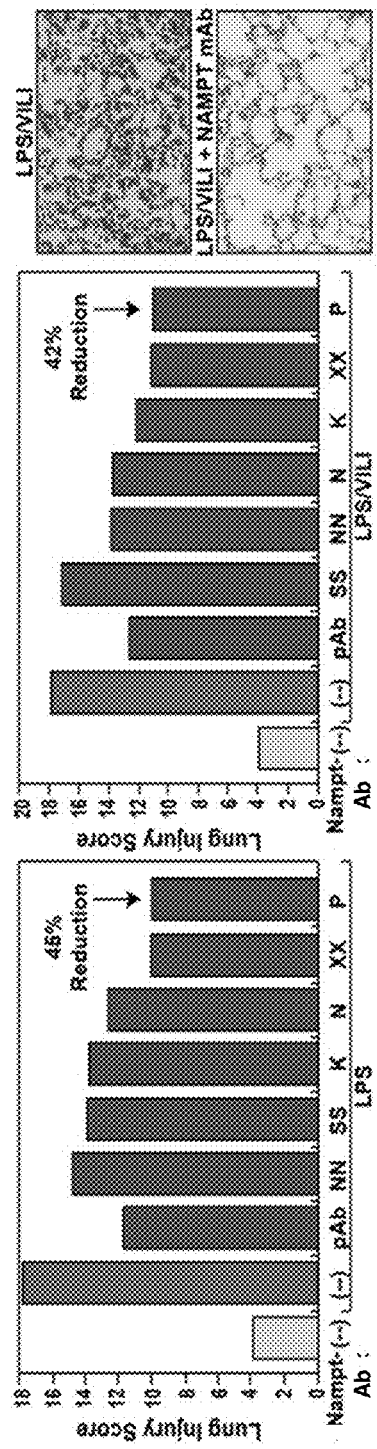
Figure 19C:
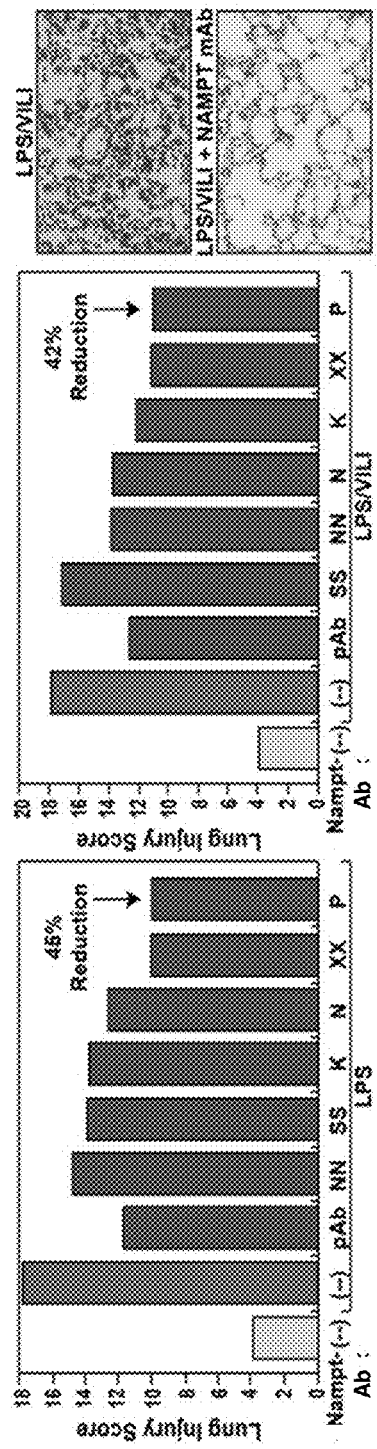
Figure 20:
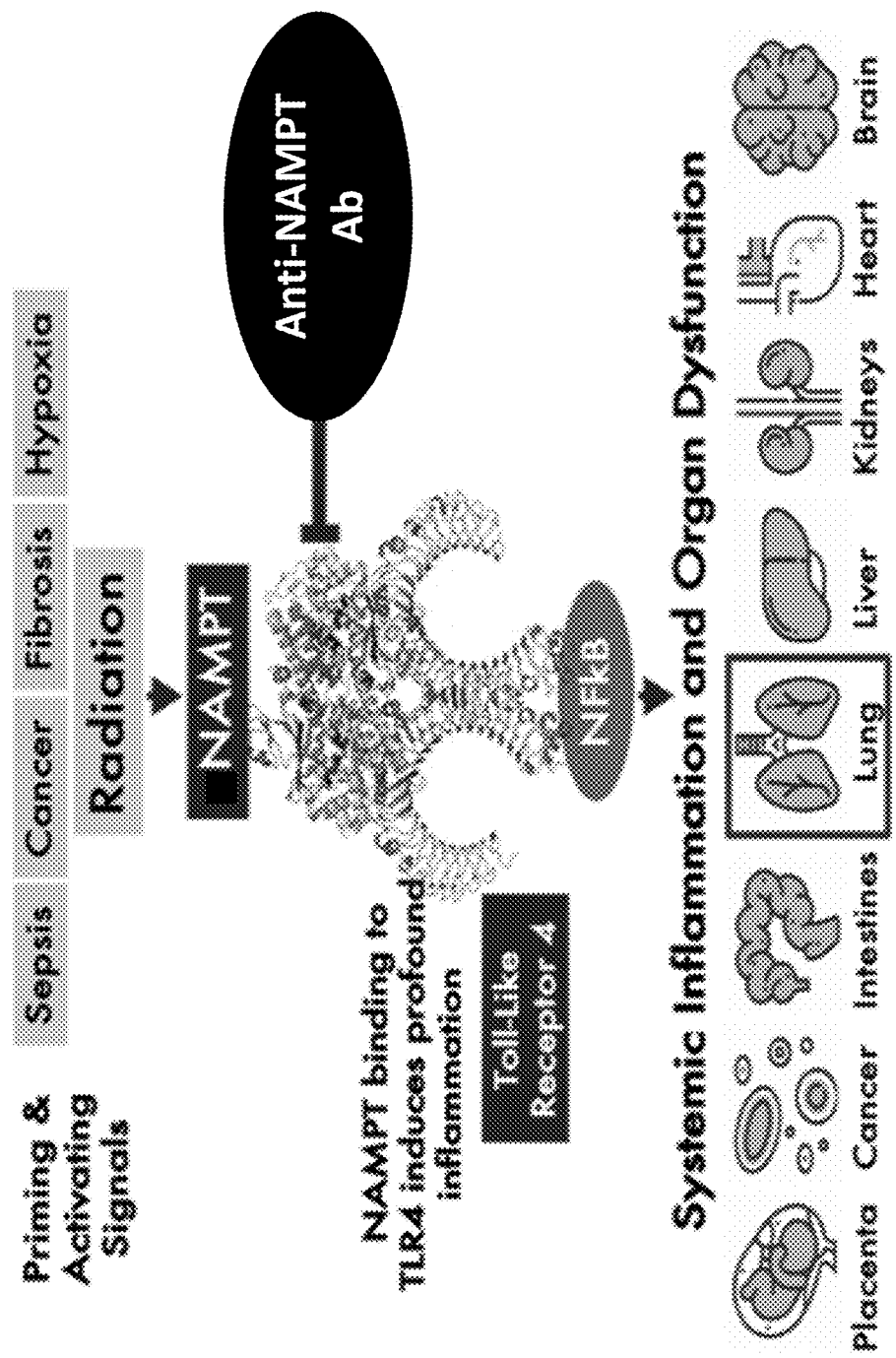
FIG. 20 is a schematic representation of the role of NAMPT in activation of systemic inflammatory cascade and multi-organ dysfunction in response to a variety of injurious stimuli, including radiation, and the potentials of anti-nAMPT antibody in alleviating such deleterious effects of NAMPT.

The results described in FIGS. 19A-19C underscore anti-NAMPT antibody as a novel, immune-based, anti-inflammatory platform. As summarized in the schematic diagram provided in FIG. 20, NAMPT is an immune effector molecule released by a variety of injurious stimuli, including radiation, that functions as a damage-associated molecular pattern protein or DAMP. Via ligation of TLR4, NAMPT contributes to activation of systemic inflammatory cascade, increased vascular permeability, and multi-organ failure. Anti-NAMPT antibody inhibits NAMPT, and thus dampens radiation-induced inflammatory cascades, lung toxicity and systemic inflammation to alleviate the symptoms of RILI.

Example 7. Radiolabeled Anti-NAMPT Antibody Identifies Increased NAMPT Expression in Inflamed Lung Tissues Radiolabeled anti-NAMPT antibodies were developed with the goal of non-invasively detecting NAMPT signaling pathway and NAMPT expression in different tissues in vivo. Imaging the mouse models with RILI using radiolabeled anti-NAMPT mAb would enable us to define the optimal time for deploying anti-NAMPT mAb as a therapeutic intervention and to survey the major organs for inflammation and cellular apoptosis, employing other specific radiolabels, following total body irradiation (TBI) or partial body irradiation (PBI), such as in a nuclear incident. A protocol was previously optimized for specifically radiolabeling antibodies with $^{99m}$Tc. With similar methodology, we radiolabeled an anti-NAMPT mAb for detection of NAMPT tissue expression in lung and other organs using an indirect labelling protocol by conjugation of the mAb with a heterobifunctional linker. To test the detection of NAMPT expression by the radiolabeled anti-NAMPT antibody, the $^{99m}$Tc-labeled anti-NAMPT mAb probe was injected into control mice and mice that were exposed to 8 Gy PBI, and biodistribution measurements and rapid autoradiograph imaging were performed. As described in FIGS. 21A-21C, higher radioactive uptake (1.8 fold higher) was observed in lung of PBI-exposed mice compared to control mice, at 2 weeks post PBI exposure. To further confirm the detection of NAMPT by the radiolabeled anti-NAMPT antibody, the $^{99m}$Tc-labeled anti-NAMPT mAb probe was injected into mice that were challenged with LPS or 20 Gy WTLI, and biodistribution measurements and rapid autoradiograph imaging were performed. As described in FIGS. 21D-21F, autoradiograph imaging showed strong detection of NAMPT expression by the $^{99m}$Tc-labeled anti-NAMPT mAb probe in lung tissues 24 hours after injection of LPS (intratracheal) and 5 days after thoracic radiation (20 Gy) in 057/B6 mice.

Thus, as described in FIGS. 21A-21F, the radiolabeled anti-NAMPT antibody was effective in detecting increased NAMPT expression in inflamed lung tissues. This underscores the potentials of utilizing the radiolabeled anti-NAMPT antibody as a tool for detection of NAMPT, which could be pivotal in using NAMPT as a biomarker in RILI by the methods described herein.

TABLE 1

SEQUENCE TABLE

| SEQUENCE IDENTIFIER | SEQUENCE |
|---|---|
| SEQ ID NO: 1 | AGTGACTTAAGCAACGGAGCGCGGTGAAGCTCATTTTTC TCCTTCCTCGCAGCCGCGCCAGGGAGCTCGCGGCGCGCG GCCCCTGTCCTCCGGCCCGAGATGAATCCTGCGGCAGAA GCCGAGTTCAACATCCTCCTGGCCACCGACTCCTACAAG GTTACTCACTATAAACAATATCCACCCAACACAAGCAAA GTTTATTCCTACTTTGAATGCCGTGAAAAGAAGACAGAA AACTCCAAATTAAGGAAGGTGAAATATGAGGAAACAGTA TTTTATGGGTTGCAGTACATTCTTAATAAGTACTTAAAA GGTAAAGTAGTAACCAAAGAGAAAATCCAGGAAGCCAAA GATGTCTACAAAGAACATTTCCAAGATGATGTCTTTAAT GAAAAGGGATGGAACTACATTCTTGAGAAGTATGATGGG CATCTTCCAATAGAAATAAAAGCTGTTCCTGAGGGCTTT GTCATTCCCAGAGGAAATGTTCTCTTCACGGTGGAAAAC ACAGATCCAGAGTGTTACTGGCTTACAAATTGGATTGAG ACTATTCTTGTTCAGTCCTGGTATCCAATCACAGTGGCC ACAAATTCTAGAGAGCAGAAGAAAATATTGGCCAAATAT TTGTTAGAAACTTCTGGTAACTTAGATGGTCTGGAATAC AAGTTACATGATTTTGGCTACAGAGGAGTCTCTTCCCAA GAGACTGCTGGCATAGGAGCATCTGCTCACTTGGTTAAC TTCAAAGGAACAGATACAGTAGCAGGACTTGCTCTAATT AAAAAATATTATGGAACGAAAGATCCTGTTCCAGGCTAT TCTGTTCCAGCAGCAGAACACAGTACCATAACAGCTTGG GGGAAAGACCATGAAAAAGATGCTTTTGAACATATTGTA ACACAGTTTTCATCAGTGCCTGTATCTGTGGTCAGCGAT AGCTATGACATTTATAATGCGTGTGAGAAAATATGGGGT GAAGATCTAAGACATTTAATAGTATCAAGAAGTACACAG GCACCACTAATAATCAGACCTGATTCTGGAAACCCTCTT GACACTGTGTTAAAGGTTTTGGAGATTTTAGGTAAGAAG TTTCCTGTTACTGAGAACTCAAAGGGTTACAAGTTGCTG CCACCTTATCTTAGAGTTATTCAAGGGGATGGAGTAGAT ATTAATACCTTACAAGAGATTGTAGAAGGCATGAAACAA AAAATGTGGAGTATTGAAAATATTGCCTTCGGTTCTGGT GGAGGTTTGCTACAGAAGTTGACAAGAGATCTCTTGAAT TGTTCCTTCAAGTGTAGCTATGTTGTAACTAATGGCCTT GGGATTAACGTCTTCAAGGACCCAGTTGCTGATCCCAAC AAAAGGTCCAAAAAGGGCCGATTATCTTTACATAGGACG CCAGCAGGGAATTTTGTTACACTGGAGGAAGGAAAAGGA GACCTTGAGGAATATGGTCAGGATCTTCTCCATACTGTC TTCAAGAATGGCAAGGTGACAAAAAGCTATTCATTTGAT GAAATAAGAAAAAATGCACAGCTGAATATTGAACTGGAA GCAGCACATCATTAGGCTTTATGACTGGGTGTGTGTTGT GTGTATGTAATACATAATGTTTATTGTACAGATGTGTGG GGTTTGTGTTTTATGATACATTACAGCCAAATTATTTGT TGGTTTATGGACATACTGCCCTTTCATTTTTTTTCTTTT CCAGTGTTTAGGTGATCTCAAATTAGGAAATGCATTTAA CCATGTAAAAGATGAGTGCTAAAGTAAGCTTTTTAGGGC CCTTTGCCAATAGGTAGTCATTCAATCTGGTATTGATCT TTTCACAAATAACAGAACTGAGAAACTTTTATATATAAC TGATGATCACATAAAACAGATTTGCATAAAATTACCATG ATTGCTTTATGTTTATATTTAACTTGTATTTTTGTACAA ACAAGATTGTGTAAGATATATTTGAAGTTTCAGTGATTT AACAGTCTTTCCAACTTTTCATGATTTTTATGAGCACAG ACTTTCAAGAAAATACTTGAAAATAAATTACATTGCCTT TTGTCCATTAATCAGCAAATAAAACATGGCCTTAACAAA GTTGTTTGTGTTATTGTACAATTTGAAAATTATGTCGGG ACATACCCTATAGAATTACTAACCTTACTGCCCCTTGTA GAATATGTATTAATCATTCTACATTAAAGAAAATAATGG TTCTTACTGGAATGTCTAGGCACTGTACAGTTATTATAT ATCTTGGTTGTTGTATTGTACCAGTGAAATGCCAAATTT GAAAGGCCTGTACTGCAATTTTATATGTCAGAGATTGCC TGTGGCTCTAATATGCACCTCAAGATTTTAAGGAGATAA TGTTTTTAGAGAGAATTTCTGCTTCCACTATAGAATATA TACATAAATGTAAAATACTTACAAAAGTGGAAGTAGTGT ATTTTAAAGTAATTACACTTCTGAATTTATTTTTCATAT TCTATAGTTGGTATGACTTAAATGAATTACTGGAGTGGG |

TABLE 1-continued

SEQUENCE TABLE

| SEQUENCE IDENTIFIER | SEQUENCE |
|---|---|
| | TAGTGAGTGTACTTAAATGTTTCAATTCTGTTATATTTT |
| | TTATTAAGTTTTTAAAAAATTAAATTGGATATTAAATTG |
| | TATGGACATCATTTATTTAATTTTAAACTGAATGCCCTCA |
| | ATAAGTAATACTGAAGCACATTCTTAAATGAAGATAAAT |
| | TATCTCCAATGAAAGCATGACATGTGTTTCAATAGAAG |
| | AATCTTAAGTTGGCTAAATTCAAAGTGCTTGACATCAAA |
| | ATGTTCTAGAGTGATTAGCTACTAGATTCTGAATCATAC |
| | ATCACATCTGACTAGAGACCAGTTTCTTTCGAATGATTC |
| | TTTTATGTATGTAGATCTGTTCTTCTGAGGCAGCGGTTG |
| | GCCAACTATAGCCCAAAGGCCAAATTTGGACTTCTTTTT |
| | ATAAATGCAGATTGTCTATGGCTGCTTTCCCACTACTCC |
| | AGCCTAAGGTAAACAGCTGAACATAGAAGCCAAATGAGAA |
| | TCGCAAAGCCCAAAATGTTTATTAACCTGCCCTTTACAC |
| | AAAATTACACAAAAAGTTTCCTGATCTCTGTTCTAAGAA |
| | AAGGAGTGTGCCTTGCATTTAAAAGGAAATGTTGGTTTC |
| | TAGGGAAGGGAGGAGGCTAAATAATTGATACGGAATTTT |
| | CCTCTTTTGTCTTCTTTTTTCTCACTTAAGAATCCGATA |
| | CTGGAAGACTGATTTAGAAAAGTTTTTAACATGACATTA |
| | AATGTGAAATTTTAAAAATTGAAAAGCCATAAATCATCT |
| | GTTTTAAATAGTTACATAGAGAAATGACTACTAGAATAA |
| | CCTAATTAGAAGTGTTATCTTCATTAAATGTTTTTTGTA |
| | AGTGGTATTAGAAAGAATATGTTTTTCAGATGGTTCTTT |
| | AAACATGTAGTGAGAACAATAAGCATTATTCACTTTTAG |
| | TAAGTCTTCTGTAATCCATGATATAAAATAATTTTAAAA |
| | TGATTTTTTAATGTATTTGAGTAAAGATGAGTAGTATTA |
| | AGAAAACACACATTTCTTCACAAAATGTGCTAAGGGGC |
| | GTGTAAAGAATCAAAAGAAACTATTACCAATAATAGTTT |
| | TGATAATCACCCATAATTTTGTGTTTAAACATTGAAATT |
| | ATAGTACGACAGTATTCTCTGTGTTCTGTGAATTTCAG |
| | CAGCTTCAGAATAGAGTTTAATTTAGAAATTTGCAGTGA |
| | AAAAAGCTATCTCTTTGTTCACAACCATAAATCAGGAGA |
| | TGGAGATTAATTCTATTGGCTCTTAGTCACTTGGAACTG |
| | ATTAATTCTGACTTTCTGTCACTAAGCACTTGGTATTTG |
| | GCCATCTCCATTCTGAGCACCAAACGGTTAACACGAATG |
| | TCCACTAGAACTCTGCTGTGTGTCACCCTTAAATCAGTC |
| | TAAATCTTCCAGACAAAAGCAAATGGCATTTATGGATTT |
| | AAGTCATTAGATTTCAACTGACATTAATTAATCCCTCT |
| | TGATTGATTATATCATCAAGTATTTATATCTTAAATAGG |
| | AGGTAGGATTTCTGTGTTAAGACTCTTATTTGTACCCTA |
| | TAATTAAAGTAAAATGTTTTTTATGAGTATCCCTTGTTT |
| | TCCCTTCTTAAATTGTTATCAAACAATTTTTATAATGAA |
| | ATCTATCTTGGAAAATTAGAAAGAAAATGGCAAGGTAT |
| | TTATTGTTCTGTTTGCCATAATTTAGAACTCACACTTAA |
| | GTATTTTGTAGTTTTACATTCCTTTTTAACCCATTCAGT |
| | GGAGAATGTCAGCTTTTCTCCCAAGTTGTATGTTAAGTC |
| | TATTCTAATATGTACTCAACATCAAGTTATAAACATGTA |
| | ATAAACATGGAAATAAAGTTTAGCTCTATTA |
| SEQ ID NO: 2 | MNPAAEAEFNILLATDSYKVTHYKQYPPNTSKVYSYFEC |
| | REKKTENSKLRKVKYEETVFYGLQYILNKYLKGKVVTKE |
| | KIQEAKDVYKEHFQDDVFNEKGWNYILEKYDGHLPIEIK |
| | AVPEGFVIPRGNVLFTVENTDPECYWLTNWIETILVQSW |
| | YPITVATNSREQKKILAKYLLETSGNLDGLEYKLHDFGY |
| | RGVSSQETAGIGASAHLVNFKGTDTVAGLALIKKYYGTK |
| | DPVPGYSVPAAEHSTITAWGKDHEKDAFEHIVTQFSSVP |
| | VSVVSDSYDIYNACEKIWGEDLRHLIVSRSTQAPLIIRP |
| | DSGNPLDTVLKVLEILGKKFPVTENSKGYKLLPPYLRVI |
| | QGDGVDINTLQEIVEGMKQKMWSIENIAFGSGGGLLQKL |
| | TRDLLNCSFKCSYVVTNGLGINVFKDPVADPNKRSKKGR |
| | LSLHRTPAGNFVTLEEGKGDLEEYGQDLLHTVFKNGKVT |
| | KSYSFDEIRKNAQLNIELEAAHH |

---

The invention claimed is:

1. A method of reducing inflammation in a human subject to address radiation-induced lung injury (RILI), said method comprising:

(a) detecting a level of nicotinamide phosphoribosyltransferase (NAMPT) in a biological sample obtained from the human subject by contacting the biological sample with a capture agent that specifically binds NAMPT;

(b) comparing the level of NAMPT to a healthy control or a reference value, wherein a higher level of NAMPT in the biological sample compared to the healthy control or the reference value is indicative of the presence of RILI in the human subject; and (c) administering to the subject a NAMPT inhibitor, the level of NAMPT in the biological sample being higher than the healthy control or reference value.

2. The method of claim 1, wherein the capture agent detects binds NAMPT protein and binding between the NAMPT protein and the capture agent is detected by autoradiography, western blot analysis, immunohistochemistry (IHC), or ELISA.

3. The method of claim 2, wherein the capture agent is an anti-NAMPT antibody.

4. The method of claim 3, wherein the anti-NAMPT antibody is radiolabeled.

5. The method of claim 1, wherein the capture agent detects NAMPT mRNA and binding between NAMPT and the capture agent is detected by RT-PCR.

6. The method of claim 5, wherein the capture agent is a primer pair complimentary to all or a portion of the nucleic acid sequence of SEQ ID NO: 1.

7. The method of claim 1, wherein the human subject shows symptoms of RILI.

8. The method of claim 1, wherein the human subject is at a risk of developing RILI.

9. The method of claim 8, wherein the human subject is a cancer patient undergoing radiotherapy.

10. The method of claim 8, wherein the human subject is exposed to ionizing radiation (IR).

11. The method of claim 9, wherein the human subject is a cancer patient undergoing thoracic radiotherapy.

12. The method of claim 1, wherein the healthy control or the reference value is a level of NAMPT expression in a control subject.

13. The method of claim 12, wherein the control subject is a subject without RILI.

14. The method of claim 13, wherein the control subject is a subject without any lung disease.

15. The method of claim 1, wherein the biological sample is a tissue sample or a plasma sample.

16. The method of claim 15, wherein the sample is a tissue sample and the tissue is lung tissue, thoracic tissue, or tonsillar tissue.

17. The method of claim 1, wherein the NAMPT inhibitor is a polypeptide inhibitor.

18. The method of claim 17, wherein the NAMPT inhibitor is an anti-NAMPT antibody.

19. The method of claim 1, wherein the NAMPT inhibitor is a nucleic acid inhibitor.

20. A method of reducing inflammation in a human subject exposed to ionizing radiation, the method comprising:
 (a) detecting a level of nicotinamide phosphoribosyltransferase (NAMPT) in a biological sample obtained from the human subject by contacting the biological sample with a capture agent that specifically binds NAMPT;
 (b) comparing the level of NAMPT to a healthy control or a reference value, wherein a higher level of NAMPT in the biological sample compared to the healthy control or the reference value is indicative of presence of radiation-induced lung injury in the human subject; and
 (c) administering to the subject an anti-NAMPT antibody, the level of NAMPT in the biological sample being higher than the healthy control or reference value.

* * * * *

SEQUENCE LISTING

<160> NUMBER OF SEQ ID NOS: 2

<210> SEQ ID NO 1
<211> LENGTH: 4360
<212> TYPE: DNA
<213> ORGANISM: Homo sapiens

<400> SEQUENCE: 1

```
agtgacttaa gcaacggagc gcggtgaagc tcattttttct ccttcctcgc agccgcgcca       60
gggagctcgc ggcgcgcggc ccctgtcctc cggcccgaga tgaatcctgc ggcagaagcc      120
gagttcaaca tcctcctggc caccgactcc tacaaggtta ctcactataa acaatatcca      180
cccaacacaa gcaaagttta ttcctacttt gaatgccgtg aaaagaagac agaaaactcc      240
aaattaagga aggtgaaata tgaggaaaca gtattttatg ggttgcagta cattcttaat      300
aagtacttaa aaggtaaagt agtaaccaaa gagaaaatcc aggaagccaa agatgtctac      360
aaagaacatt tccaagatga tgtctttaat gaaaagggat ggaactacat tcttgagaag      420
tatgatgggc atcttccaat agaaataaaa gctgttcctg agggctttgt cattcccaga      480
ggaaatgttc tcttcacggt ggaaaacaca gatccagagt gttactggct tacaaattgg      540
attgagacta ttcttgttca gtcctggtat ccaatcacag tggccacaaa ttctagagag      600
cagaagaaaa tattggccaa atatttgtta gaaacttctg gtaacttaga tggtctggaa      660
tacaagttac atgattttgg ctacagagga gtctcttccc aagagactgc tggcatagga      720
gcatctgctc acttggttaa cttcaaagga acagatacag tagcaggact tgctctaatt      780
aaaaaatatt atggaacgaa agatcctgtt ccaggctatt ctgttccagc agcagaacac      840
```

```
agtaccataa cagcttgggg gaaagaccat gaaaaagatg cttttgaaca tattgtaaca    900
cagttttcat cagtgcctgt atctgtggtc agcgatagct atgacattta taatgcgtgt    960
gagaaaatat ggggtgaaga tctaagacat ttaatagtat caagaagtac acaggcacca   1020
ctaataatca gacctgattc tggaaaccct cttgacactg tgttaaaggt tttggagatt   1080
ttaggtaaga agtttcctgt tactgagaac tcaaagggtt acaagttgct gccaccttat   1140
cttagagtta ttcaagggga tggagtagat attaatacct acaagagat tgtagaaggc    1200
atgaaacaaa aaatgtggag tattgaaaat attgccttcg gttctggtgg aggtttgcta   1260
cagaagttga caagagatct cttgaattgt tccttcaagt gtagctatgt tgtaactaat   1320
ggccttggga ttaacgtctt caaggaccca gttgctgatc ccaacaaaag gtccaaaaag   1380
ggccgattat ctttacatag gacgccagca gggaattttg ttacactgga ggaaggaaaa   1440
ggagaccttg aggaatatgg tcaggatctt ctccatactg tcttcaagaa tggcaaggtg   1500
acaaaaagct attcatttga tgaaataaga aaaaatgcac agctgaatat tgaactggaa   1560
gcagcacatc attaggcttt atgactgggt gtgtgttgtg tgtatgtaat acataatgtt   1620
tattgtacag atgtgtgggg tttgtgtttt atgatacatt acagccaaat tatttgttgg   1680
tttatggaca tactgccctt tcattttttt tcttttccag tgtttaggtg atctcaaatt   1740
aggaaatgca tttaaccatg taaaagatga gtgctaaagt aagcttttta gggccctttg   1800
ccaataggta gtcattcaat ctggtattga tcttttcaca ataacagaa ctgagaaact    1860
tttatatata actgatgatc acataaaaca gatttgcata aaattaccat gattgcttta   1920
tgtttatatt taacttgtat ttttgtacaa acaagattgt gtaagatata tttgaagttt   1980
cagtgattta acagtctttc caacttttca tgatttttat gagcacagac tttcaagaaa   2040
atacttgaaa ataaattaca ttgccttttg tccattaatc agcaaataaa acatggcctt   2100
aacaaagttg tttgtgttat tgtacaattt gaaaattatg tcgggacata ccctatagaa   2160
ttactaacct tactgcccct tgtagaatat gtattaatca ttctacatta aagaaaataa   2220
tggttcttac tggaatgtct aggcactgta cagttattat atatcttggt tgttgtattg   2280
taccagtgaa atgccaaatt tgaaaggcct gtactgcaat tttatatgtc agagattgcc   2340
tgtggctcta atatgcacct caagatttta aggagataat gttttagag agaatttctg    2400
cttccactat agaatatata cataaatgta aaatacttac aaaagtgaa gtagtgtatt    2460
ttaaagtaat tacacttctg aatttatttt tcatattcta tagttggtat gacttaaatg   2520
aattactgga gtgggtagtg agtgtactta aatgtttcaa ttctgttata ttttttatta   2580
agttttaaa aaattaaatt ggatattaaa ttgtatggac atcatttatt aattttaaac    2640
tgaatgccct caataagtaa tactgaagca cattcttaaa tgaagataaa ttatctccaa   2700
tgaaaagcat gacatgtgtt tcaatagaag aatcttaagt tggctaaatt caaagtgctt   2760
gacatcaaaa tgttctagag tgattagcta ctagattctg aatcatacat cacatctgac   2820
tagagaccag tttctttcga atgattcttt tatgtatgta gatctgttct tctgaggcag   2880
cggttggcca actatagccc aaaggccaaa tttggacttc ttttttataaa tgcagattgt  2940
ctatggctgc tttcccacta ctccagccta aggtaaacag ctgcaataga agccaaatga   3000
gaatcgcaaa gcccaaaatg tttattaacc tgcccttta acaaaattac acaaaaagtt    3060
tcctgatctc tgttctaaga aaaggagtgt gccttgcatt taaaaggaaa tgttggtttc   3120
tagggaaggg aggaggctaa ataattgata cggaattttc tcttttgtc ttctttttc     3180
tcacttaaga atccgatact ggaagactga tttagaaaag ttttaacat gacattaaat    3240
```

```
gtgaaatttt aaaaattgaa aagccataaa tcatctgttt taaatagtta catgagaaaa    3300
tgatcactag aataacctaa ttagaagtgt tatcttcatt aaatgttttt tgtaagtggt    3360
attagaaaga atatgttttt cagatggttc tttaaacatg tagtgagaac aataagcatt    3420
attcactttt agtaagtctt ctgtaatcca tgatataaaa taattttaaa atgattttt     3480 aatgtatttg agtaaagatg agtagtatta agaaaacac  acatttcttc acaaaatgtg    3540
ctaaggggcg tgtaaagaat caaaagaaac tattaccaat aatagttttg ataatcaccc    3600
ataattttgt gtttaaacat tgaaattata gtacagacag tattctctgt gttctgtgaa    3660
tttcagcagc ttcagaatag agtttaattt agaaatttgc agtgaaaaaa gctatctctt    3720
tgttcacaac cataaatcag gagatggaga ttaattctat tggctcttag tcacttggaa    3780
ctgattaatt ctgactttct gtcactaagc acttggtatt tggccatctc cattctgagc    3840
accaaacggt taacacgaat gtccactaga actctgctgt gtgtcaccct taaatcagtc    3900
taaatcttcc agacaaaagc aaatggcatt tatggattta agtcattaga ttttcaactg    3960
acattaatta atccctcttg attgattata tcatcaagta tttatatctt aaataggagg    4020
taggatttct gtgttaagac tcttatttgt acccctataat taaagtaaaa tgttttttat    4080
gagtatccct tgttttccct tcttaaattg ttatcaaaca attttttataa tgaaatctat    4140 cttggaaaat tagaaagaaa aatggcaagg tatttattgt tctgtttgcc ataatttaga    4200
actcacactt aagtattttg tagttttaca ttccttttta acccattcag tggagaatgt    4260
cagcttttct cccaagttgt atgttaagtc tattctaata tgtactcaac atcaagttat    4320
aaacatgtaa taaacatgga aataaagttt agctctatta                         4360

<210> SEQ ID NO 2
<211> LENGTH: 491
<212> TYPE: PRT
<213> ORGANISM: Homo sapiens

<400> SEQUENCE: 2

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
                20                  25                  30

Val Tyr Ser Tyr Phe Glu Cys Arg Glu Lys Thr Glu Asn Ser Lys
            35                  40                  45

Leu Arg Lys Val Lys Tyr Glu Glu Thr Val Phe Tyr Gly Leu Gln Tyr
        50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175
```

```
Leu Glu Thr Ser Gly Asn Leu Asp Gly Leu Glu Tyr Lys Leu His Asp
            180                 185                 190

Phe Gly Tyr Arg Gly Val Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
            275                 280                 285

Lys Ile Trp Gly Glu Asp Leu Arg His Leu Ile Val Ser Arg Ser Thr
290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
            325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
    450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
            485                 490
```